United States Patent
Dejima

(10) Patent No.: US 10,092,173 B2
(45) Date of Patent: Oct. 9, 2018

(54) ENDOSCOPIC SURGICAL DEVICE, OVERTUBE, AND ENDOSCOPE

(71) Applicant: FUJIFILM Corporation, Tokyo (JP)

(72) Inventor: Takumi Dejima, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/059,277

(22) Filed: Mar. 2, 2016

(65) Prior Publication Data

US 2016/0174825 A1 Jun. 23, 2016

Related U.S. Application Data

(63) Continuation of application No. PCT/JP2014/072992, filed on Sep. 2, 2014.
(Continued)

(51) Int. Cl.
*A61B 1/00* (2006.01)
*A61B 1/018* (2006.01)
(Continued)

(52) U.S. Cl.
CPC .......... *A61B 1/018* (2013.01); *A61B 1/00087* (2013.01); *A61B 1/00135* (2013.01);
(Continued)

(58) Field of Classification Search
CPC ....... A61B 1/01; A61B 1/018; A61B 1/00128; A61B 1/00135; A61B 17/3421;
(Continued)

(56) References Cited

U.S. PATENT DOCUMENTS

| 4,538,594 A | 9/1985 | Boebel et al. |
| 5,569,205 A | 10/1996 | Hart et al. |

(Continued)

FOREIGN PATENT DOCUMENTS

| JP | 2002-330928 | 11/2002 |
| JP | 2003-088532 | 3/2003 |

(Continued)

OTHER PUBLICATIONS

"Written Opinion of the International Searching Authority of PCT/JP2014/072992", this report contains the following items: Form PCT/ISA237 (cover sheet), PCT/ISA237 (Box No. I), PCT/ISA237 (Box No. III),PCT/ISA237 (Box No. V) and PCT/ISA237 (Box No. VI), dated Oct. 14, 2014, with English translation thereof, pp. 1-10.

(Continued)

*Primary Examiner* — Timothy J Neal
*Assistant Examiner* — Aaron B Fairchild
(74) *Attorney, Agent, or Firm* — JCIPRNET

(57) ABSTRACT

The overtube includes a slider within an overtube body, which guides an endoscope and a treatment tool. An endoscope-coupled part and a treatment tool-coupled part are provided inside the slider, and the slider has a dead zone where the forward and backward movement of either the endoscope or the treatment tool does not interlock with the movement of the other and a sensing zone where the forward and backward movement of either the endoscope or the treatment tool interlocks with the movement of the other. The overtube body includes a distal-end-side stopper and a base-end-side stopper that restrict the movable range of the slider. A length L from a coupling position of the endoscope to a distal end position of the overtube body and a length Ls from the coupling position of the endoscope to a distal end position of the endoscope are set to satisfy Ls≥L.

14 Claims, 29 Drawing Sheets

Related U.S. Application Data

(60) Provisional application No. 61/873,107, filed on Sep. 3, 2013.

(51) Int. Cl.
   *A61B 17/34* (2006.01)
   *A61B 17/22* (2006.01)
   *A61B 1/313* (2006.01)
   *A61B 90/00* (2016.01)

(52) U.S. Cl.
   CPC ...... *A61B 1/00154* (2013.01); *A61B 1/00174* (2013.01); *A61B 17/3421* (2013.01); *A61B 1/313* (2013.01); *A61B 17/3474* (2013.01); *A61B 90/37* (2016.02); *A61B 2017/22074* (2013.01); *A61B 2017/3445* (2013.01); *A61B 2017/3456* (2013.01)

(58) Field of Classification Search
   CPC .............. A61B 1/0008; A61B 1/00177; A61B 2017/0477; A61B 1/0014; A61B 1/00154; A61B 2017/3445; A61B 2017/3447; A61B 2017/3449; A61B 2017/3466; A61B 1/00142; A61B 2017/3462; A61B 2017/00477; A61B 2017/3409; A61M 39/22; A61M 25/0662; A61M 2025/0681
   See application file for complete search history.

(56) References Cited

U.S. PATENT DOCUMENTS

| | | | | |
|---|---|---|---|---|
| 5,634,911 | A * | 6/1997 | Hermann | A61B 17/3417 604/246 |
| 6,315,714 | B1 * | 11/2001 | Akiba | A61B 1/00135 600/114 |
| 2001/0049497 | A1 | 12/2001 | Kalloo et al. | |
| 2003/0055437 | A1 | 3/2003 | Yasunaga | |
| 2003/0135091 | A1 | 7/2003 | Nakazawa et al. | |
| 2005/0119525 | A1 * | 6/2005 | Takemoto | A61B 1/00154 600/114 |
| 2005/0222495 | A1 | 10/2005 | Okada et al. | |
| 2008/0287963 | A1 * | 11/2008 | Rogers | A61B 1/00039 606/130 |
| 2009/0093752 | A1 | 4/2009 | Richard et al. | |
| 2009/0259172 | A1 | 10/2009 | Yamaoka et al. | |
| 2010/0016659 | A1 | 1/2010 | Weitzner | |
| 2010/0198006 | A1 | 8/2010 | Greenburg et al. | |
| 2011/0124960 | A1 | 5/2011 | St. Onge et al. | |
| 2011/0184231 | A1 | 7/2011 | Page et al. | |
| 2011/0230713 | A1 | 9/2011 | Kleemann | |
| 2011/0282155 | A1 * | 11/2011 | Kase | A61B 1/0615 600/165 |
| 2015/0080650 | A1 | 3/2015 | Dejima et al. | |
| 2016/0174825 | A1 | 6/2016 | Dejima | |

FOREIGN PATENT DOCUMENTS

| | | |
|---|---|---|
| JP | 2003-325436 | 11/2003 |
| JP | 2004-041580 | 2/2004 |
| JP | 2004-141486 | 5/2004 |
| JP | 2004-180858 | 7/2004 |
| JP | 2005152416 | 6/2005 |
| JP | 2005-192707 | 7/2005 |
| JP | 2005-287963 | 10/2005 |
| JP | 2011-528576 | 11/2011 |
| JP | 2012-501695 | 1/2012 |
| JP | 2012-505055 | 3/2012 |
| WO | 2010042913 | 4/2010 |
| WO | 2011014711 | 2/2011 |
| WO | 2013176167 | 11/2013 |
| WO | 2015033908 | 3/2017 |

OTHER PUBLICATIONS

"Office Action of Japan Counterpart Application," with machine English translation thereof, dated Apr. 16, 2018, p. 1-p. 8.

"Written Opinion of the International Searching Authority of PCT/JP2014/072988", this report contains the following items: Form PCT/ISA237 (cover sheet), PCT/ISA237 (Box No. I), PCT/ISA237 (Box No. V) and PCT/ISA237 (Box No. VI), dated Oct. 28, 2014, with a partial English translation thereof, pp. 1-8.

"Office Action of U.S. Appl. No. 15/058,176," dated Sep. 27, 2016, p.1 -p. 14.

"Office Action of U.S. Appl. No. 15/058,176," dated May 3, 2017, p. 1-p. 28.

"Office Action of Japan Counterpart Application," with English translation thereof, dated May 24, 2017, p. 1-p. 6.

"Office Action of U.S. Appl. No. 15/058,176," dated Dec. 20, 2017, p. 1-p. 15.

"Written Opinion of the International Searching Authority (Form PCT/ISA/237)" of PCT/JP2014/072989, dated Oct. 28, 2014, with English translation thereof, pp. 1-10.

"Office Action of U.S. Appl. No. 15/058,164," dated Sep. 29, 2016, p. 1-p. 15.

"Office Action of U.S. Appl. No. 15/058,164," dated Apr. 24, 2017, p. 1-p. 32.

"Office Action of U.S. Appl. No. 15/058,164," dated Dec. 19, 2017, p. 1-p. 17.

"Written Opinion of the International Searching Authority of PCT/JP2014/072991", this report contains the following items: Form PCT/ISA237(cover sheet), PCT/ISA237(Box No. I), PCT/ISA237(Box No. V) and PCT/ISA237(Box No. VI), dated Oct. 14, 2014, which is English translation of "Written Opinion of the International Searching Authority", pp. 1-8.

"Office Action of U.S. Appl. No. 15/058,111," dated Sep. 27, 2016, p. 1-p. 19.

"Office Action of U.S. Appl. No. 15/058,111," dated May 5, 2017, p. 1-p. 32.

"Office Action of U.S. Appl. No. 15/058,111," dated Dec. 21, 2017, p. 1-p. 19.

* cited by examiner

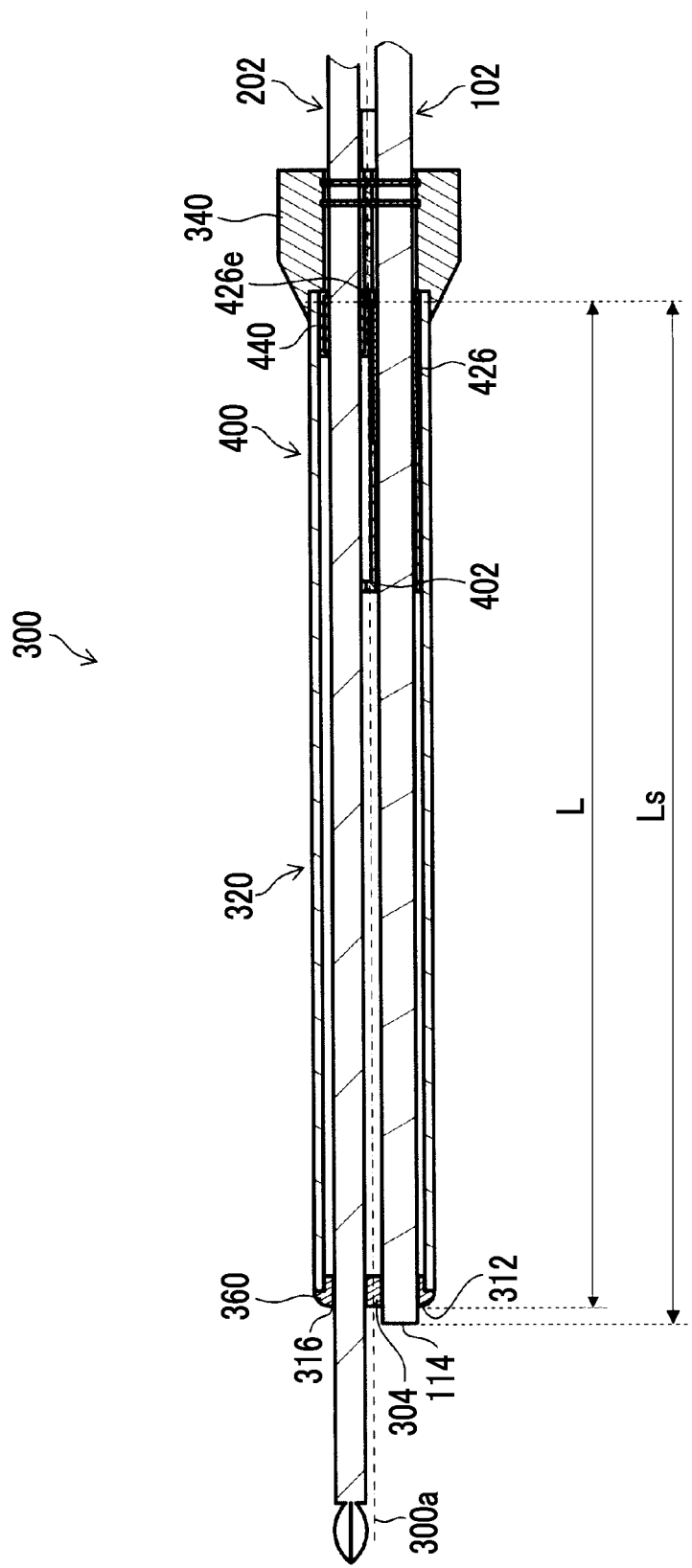

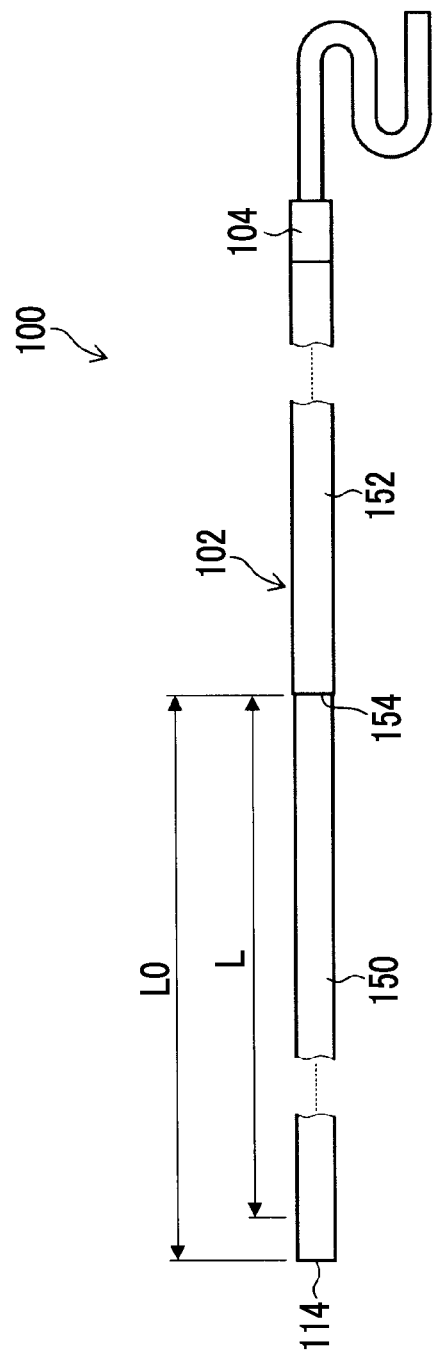

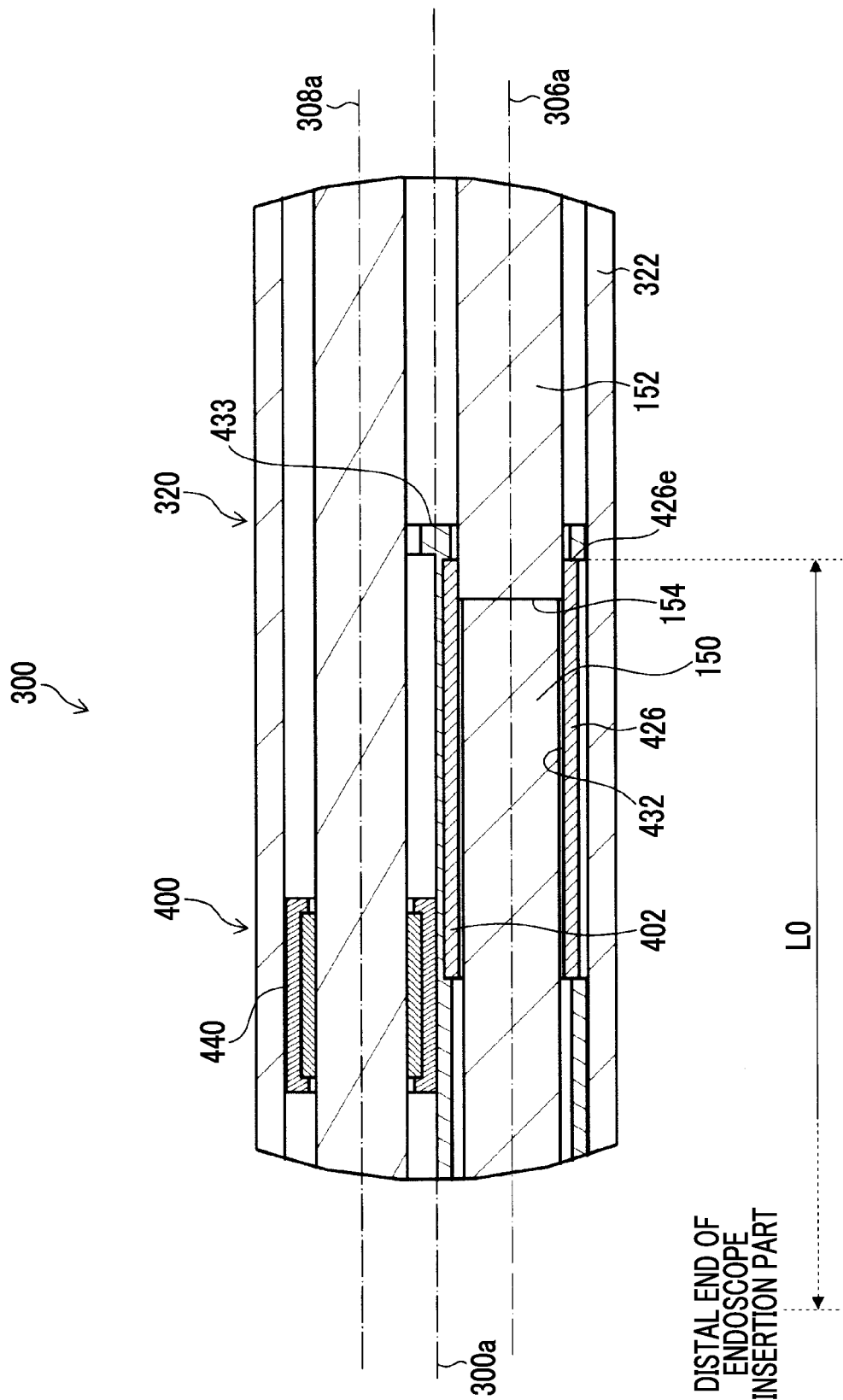

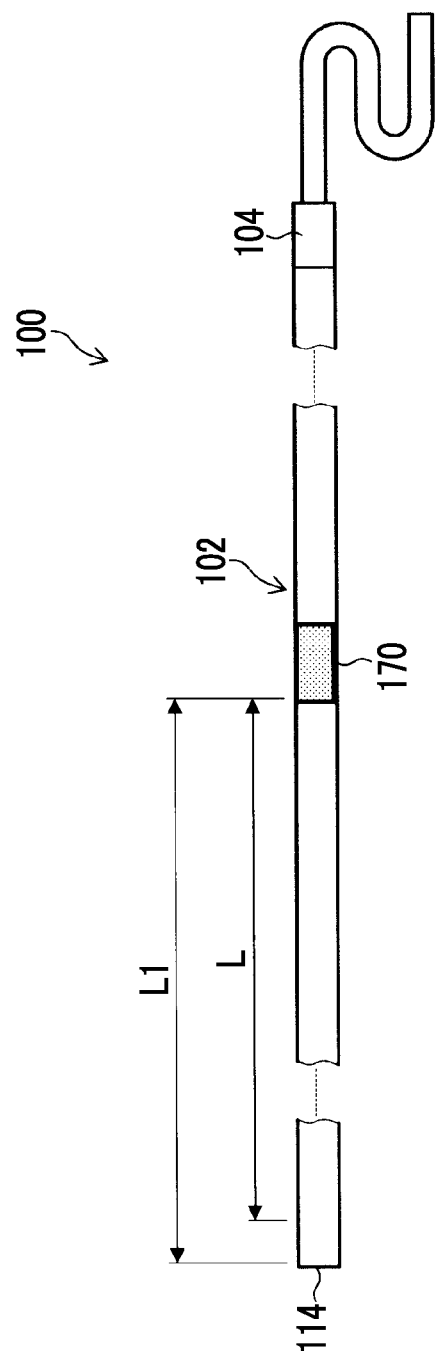

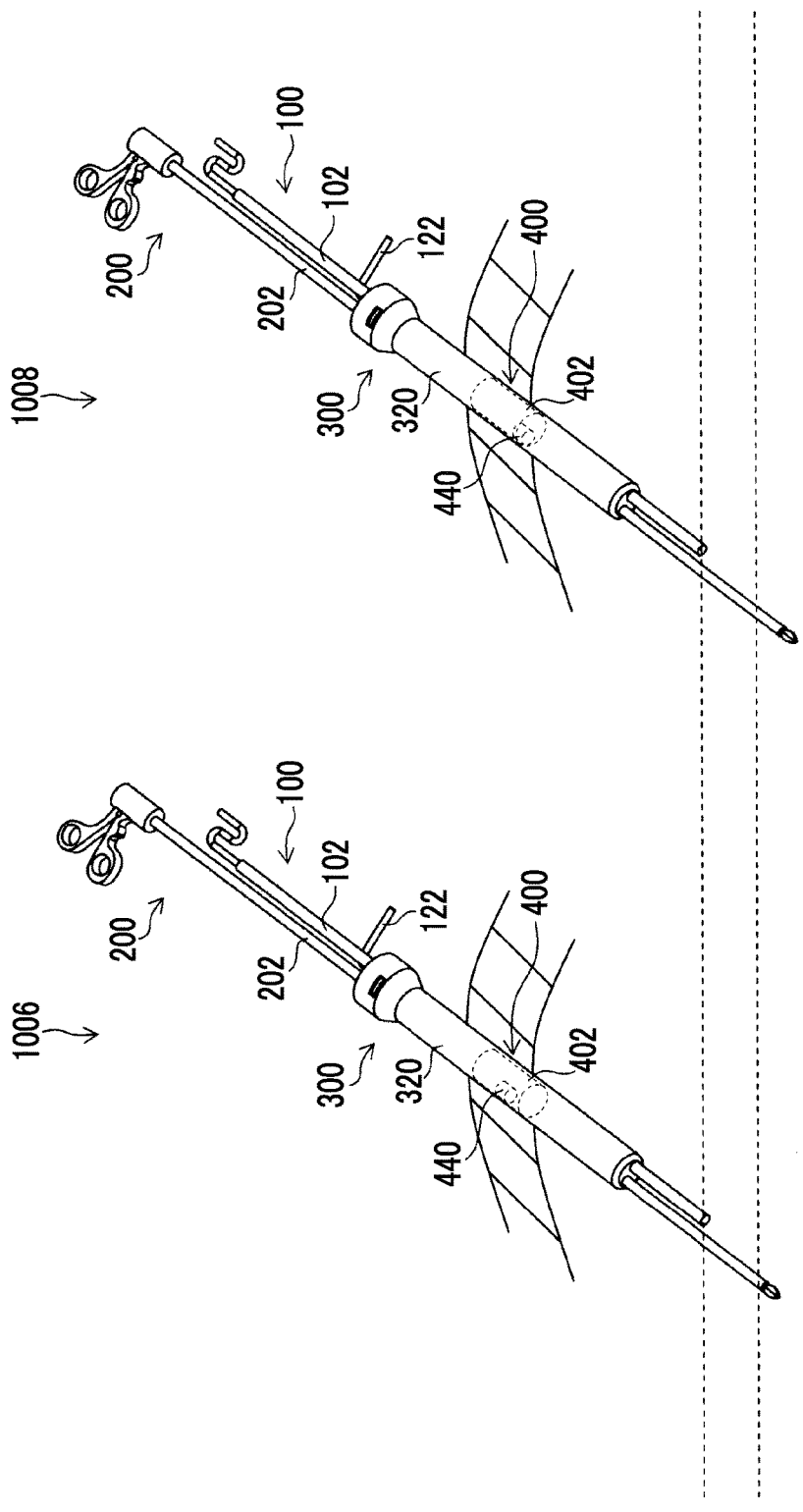

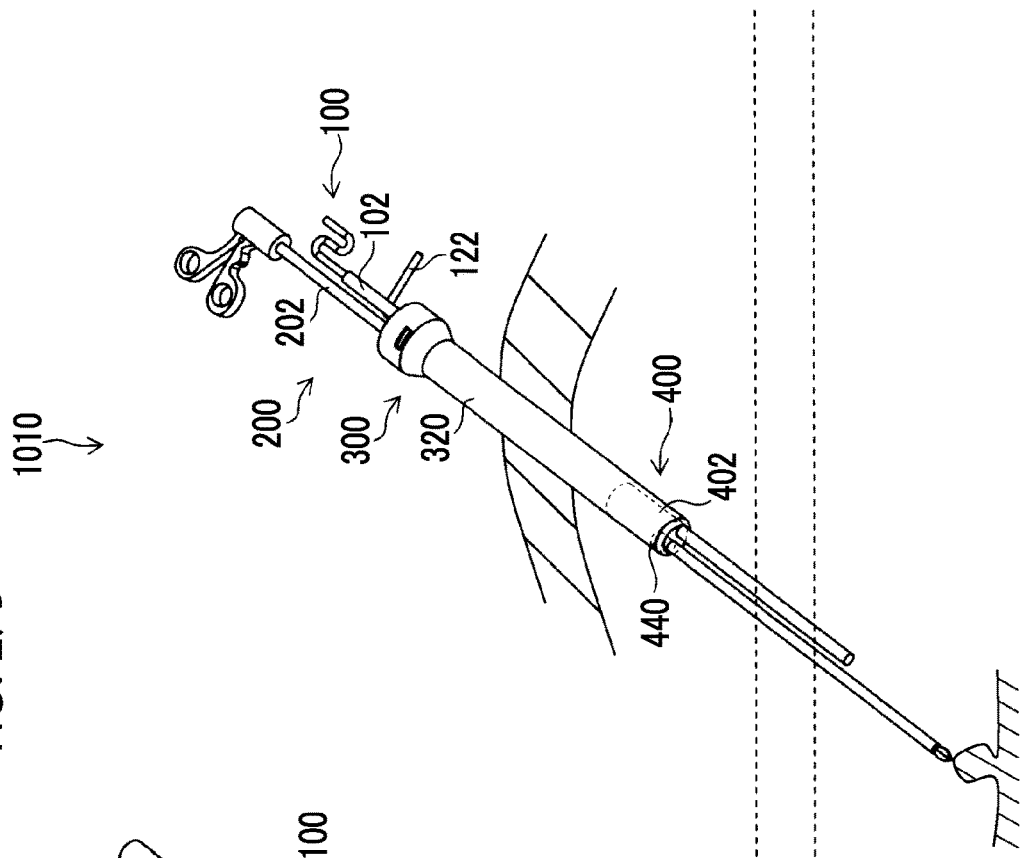
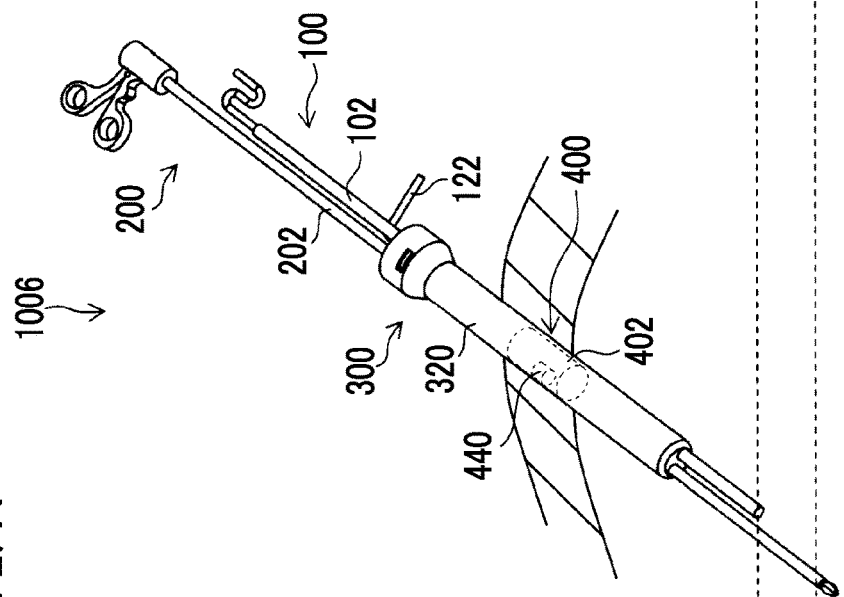

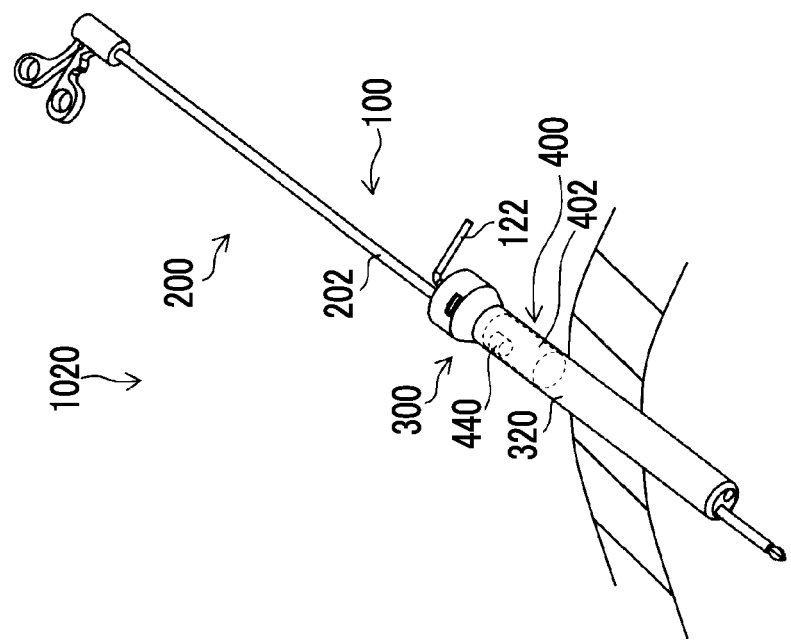
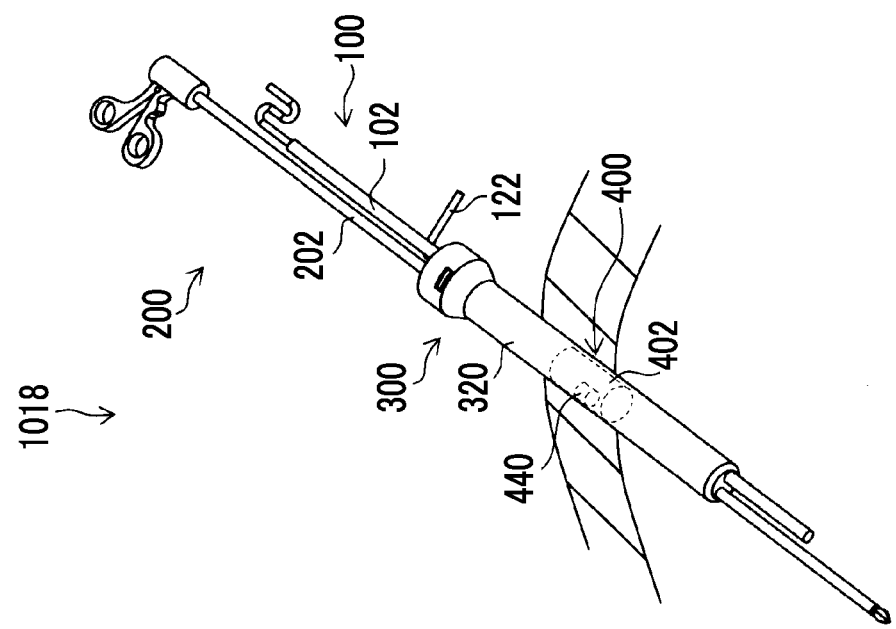

ENDOSCOPIC SURGICAL DEVICE, OVERTUBE, AND ENDOSCOPE

CROSS-REFERENCE TO RELATED APPLICATIONS

The present application is a Continuation of PCT International Application No. PCT/JP2014/072992 filed on Sep. 2, 2014 claiming priority under 35 U.S.C. § 119(a) of U.S. Provisional Application 61/873,107 filed on Sep. 3, 2013. Each of the above applications is hereby expressly incorporated by reference, in their entirety, into the present application.

BACKGROUND OF THE INVENTION

1. Field of the Invention

The present invention relates to an endoscopic surgical device, an overtube (outer sleeve), and an endoscope, and particularly, relates to an endoscopic surgical device, an overtube, and an endoscope that can operate in a state where an endoscope and a treatment tool inserted into a body cavity are interlocked with each other.

2. Description of the Related Art

In the related art, the endoscopic surgery of inserting a treatment tool and an endoscope into a patient's body cavity and performing treatment work while observing, using the endoscope, the treatment state of an affected part using the treatment tool inserted into the body cavity has been known. In this surgery, in order for a surgeon to obtain a visual field where surgery is easy, the operation of changing the observation position of the endoscope is performed when necessary.

Generally, in the endoscopic surgery, a surgeon's hand is blocked due to the operation of the treatment tool, and the operation of changing the observation position of the endoscope is performed by an assistant called a scopist (endoscopic technician). For this reason, when the observation position of the endoscope is changed, the surgeon should serially give instructions to the assistant. Therefore, the work of correctly directing the orientation of the endoscope to a direction desired by the surgeon is difficult, and stress is likely to be imposed on the surgeon. Additionally, since the assistant performs an operation after the surgeon issues an instruction, there is a tendency that surgery time is likely to be prolonged. Additionally, the assistant should operate the endoscope so as not to interfere with a surgeon's procedure, and the operation is likely to become complicated.

In contrast, various techniques of interlocking the endoscope and the treatment tool have been suggested up to now (for example, refer to JP2004-141486A and JP2003-325436A).

An endoscopic surgery system that moves the treatment tool while following the fluctuation of the visual field of the endoscope is disclosed in JP2004-141486A. In this endoscopic surgery system, a treatment part of the treatment tool is kept from deviating from the visual field of the endoscope by detecting the movement distance (the rotational angle and the amount of insertion and extraction) of the endoscope in a state where the endoscope and the treatment tool have been inserted into an integral sheath (guide member), and controlling the movement distance (the rotational angle and the amount of insertion and extraction) of the treatment tool with respect to the sheath on the basis of the detection result.

Additionally, an endoscopic surgery device that changes the visual field of the endoscope while following the movement of the treatment tool inserted into the body cavity during the endoscopic surgery is disclosed in JP2003-325436A. This endoscopic surgery device is provided by mechanically coupling the treatment tool to a distal end part of the endoscope to integrally move the treatment tool and the distal end part of the endoscope to move the observation optical axis of the endoscope in a direction in which the treatment tool moves.

SUMMARY OF THE INVENTION

Under the above background, in the endoscopic surgery, it is desired that the visual field of the endoscope can be easily changed while the surgeon operates the treatment tool without asking for an assistant's help.

However, the endoscopic surgery system disclosed in JP2004-141486A does not mechanically interlock the endoscope with the treatment tool, and has a problem in which a mechanism for performing interlocking control of the endoscope and the treatment tool is easily enlarged and complicated. Additionally, this endoscopic surgery system moves the treatment tool while following the movement of the endoscope, and does not move the endoscope while following the movement of the treatment tool. For this reason, there are problems in that it is necessary to ask for an assistant's help in order to change the visual field of the endoscope, the operation for changing the observation position of the endoscope as intended by a surgeon easily becomes complicated, and the surgery time is easily prolonged.

Additionally, since the endoscopic surgery device disclosed in JP2003-325436A has a configuration in which the endoscope and the treatment tool are mechanically coupled and always move integrally, the visual field of the endoscope also changes minutely in an interlocking manner with minute movement of the treatment tool. For this reason, there is a problem in that an observation image obtained by the endoscope moves minutely and is hardly seen. Particularly when the endoscope and the treatment tool are inserted into the body cavity in a parallel state, there is a problem in which the size of an object to be observed changes in an interlocking manner with the minute movement of the treatment tool, and a sense of perspective cannot be easily held.

Additionally, in a case where a configuration in which the treatment tool and the endoscope are integrated within the overtube and the forward and backward movement of the treatment tool and the forward and backward movement of the endoscope are interlocked with each other is adopted, there is a possibility that the distal end part of the endoscope may enter the inside of the overtube when the endoscope moves forward and backward in an interlocking manner with the forward and backward movement of the treatment tool. If the distal end of the endoscope enters the inside of the overtube, the observation visual field of the endoscope is blocked by the overtube, and a malfunction such that treatment cannot be performed occurs. JP2004-141486A and JP2003-325436A do not consider about such problems at all and also do not disclose or imply means for solving the problems.

In this way, in any of the related-art techniques, there are various problems in order to smoothly perform the endoscopic surgery, and it cannot be said that the techniques of interlocking the endoscope and the treatment tool inserted into the body cavity are sufficient.

The invention has been made in view of such a situation and an object thereof is to provide an endoscopic surgical device, an overtube, and an endoscope with which a distal end of the endoscope does not enter the inside of an overtube, a surgeon can easily obtain a desired image and operability is high.

In order to achieve the above object, an endoscopic surgical device related to a first aspect of the invention is an endoscopic surgical device including an endoscope that observes the inside of a body cavity; a treatment tool that inspects or treats an affected part within the body cavity; and an overtube that guides the endoscope and the treatment tool into the body cavity. The overtube includes an overtube body that passes through a body wall and is inserted into the body cavity, an endoscope insertion passage that is provided inside the overtube body and allows the endoscope to be inserted therethrough so as to be movable forward and backward, a treatment tool insertion passage that is provided inside the overtube body and allows the treatment tool to be inserted therethrough so as to be movable forward and backward, and an interlocking member that is configured to be movable forward and backward inside the overtube body, has an endoscope-coupled part to be coupled the endoscope inserted through the endoscope insertion passage and a treatment tool-coupled part to be coupled the treatment tool inserted through the treatment tool insertion passage, and has a dead zone where the forward and backward movement of either the endoscope or the treatment tool does not interlock with the movement of the other and a sensing zone where the forward and backward movement of either the endoscope or the treatment tool interlocks with the movement of the other. The overtube body includes a distal-end-side stopper that restricts the forward and backward movement of the interlocking member to a distal end side, and a base-end-side stopper that restricts the forward and backward movement of the interlocking member with respect to a base end side. In a state where the interlocking member has abutted against the base-end-side stopper and the forward and backward movement of the interlocking member to the base end side has been restricted, when a length from a coupling position of the endoscope, to which the endoscope-coupled part is coupled, to a distal end position of the overtube body in an axial direction of the overtube body is defined as L and a length from the coupling position to a distal end position of the endoscope is defined as Ls, the coupling position is set so as to satisfy the following formula.

$$Ls \geq L$$

In the first aspect of the invention, it is preferable that the endoscope includes a smaller-diameter part that is arranged on the distal end side, and a larger-diameter part that is connected to the base end side of the smaller-diameter part, the smaller-diameter part is configured to be non-engageable with the endoscope-coupled part, and the larger-diameter part is configured to be engageable with the endoscope-coupled part.

Additionally, in the first aspect of the invention, it is preferable that the endoscope-coupled part is provided with a frictional engagement part that frictionally engages with the larger-diameter part.

Additionally, in the first aspect of the invention, it is preferable that the endoscope is made of a high-friction member having a higher frictional coefficient at the coupling position than at other positions where the endoscope-coupled part is not coupled, and the endoscope-coupled part is made of a frictional engagement part that frictionally engages with the high-friction member.

Additionally, in the first aspect of the invention, it is preferable that the interlocking member includes a slider member that is coupled to the endoscope and moves forward and backward integrally with the endoscope, and a sleeve member that is coupled to the treatment tool and moves forward and backward integrally with the treatment tool, and a range where the sleeve member is movable forward and backward with respect to the slider member is limited.

Additionally, in the first aspect of the invention, it is preferable that the sleeve member is configured so as to be rotatable around the axis with respect to the slider member.

Additionally, in the first aspect of the invention, it is preferable that the slider member is configured so as to be non-rotatable around the axis with respect to the overtube body.

Additionally, in the first aspect of the invention, it is preferable that the following formula is satisfied when a fixing force for fixing the endoscope-coupled part to the endoscope is defined as F1 and a fixing force for fixing the treatment tool-coupled part to the treatment tool is defined as F2.

$$F1 > F2$$

Additionally, in the first aspect of the invention, it is preferable that the endoscopic surgical device further includes a first valve member that is provided in the endoscope insertion passage and secures airtightness within the body cavity; and a second valve member that is provided in the treatment tool insertion passage and secures airtightness within the body cavity, and the following formulas are satisfied when a fixing force for fixing the endoscope-coupled part to the endoscope is defined as F1, a fixing force for fixing the treatment tool-coupled part to the treatment tool is defined as F2, and a frictional force that the endoscope receives from the first valve member when the endoscope moves forward and backward is defined as F3.

$$F1 > F3$$

$$F2 > F3$$

An overtube related to a second aspect of the invention is an endoscopic surgical device including an overtube body that passes through a body wall and is inserted into a body cavity, an endoscope insertion passage that is provided inside the overtube body and allows an endoscope for observing the inside of the body cavity to be inserted therethrough so as to be movable forward and backward, a treatment tool insertion passage that is provided inside the overtube body and allows a treatment tool for inspecting or treating an affected part within the body cavity to be inserted therethrough so as to be movable forward and backward, and an interlocking member that is configured to be movable forward and backward inside the overtube body, has an endoscope-coupled part to be coupled the endoscope inserted through the endoscope insertion passage and a treatment tool-coupled part to be coupled the treatment tool inserted through the treatment tool insertion passage, and has a dead zone where the forward and backward movement of either the endoscope or the treatment tool does not interlock with the movement of the other and a sensing zone where the forward and backward movement of either the endoscope or the treatment tool interlocks with the movement of the other. The overtube body includes a distal-end-side stopper that restricts the forward and backward movement of the interlocking member to a distal end side, and a base-end-side stopper that restricts the forward and backward movement of the interlocking member with respect to a base end side. In a state where the interlocking member has abutted against the base-end-side stopper and the forward and backward movement of the interlocking member to the base end side has been restricted, when a length from a coupling position of the endoscope, to which the endoscope-coupled part is coupled, to a distal end position of the overtube body in an axial direction of the overtube body is defined as L and a length from the coupling position to a distal end position of the endoscope is defined as Ls, the coupling position is set so as to satisfy the following formula.

$$Ls \geq L$$

Additionally, in the second aspect of the invention, it is preferable that the endoscope includes a smaller-diameter part that is arranged on the distal end side, and a larger-diameter part that is connected to the base end side of the smaller-diameter part, the endoscope-coupled part is configured to be non-engageable with the smaller-diameter part, and the larger-diameter part is configured to be engageable with the endoscope-coupled part.

Additionally, in the second aspect of the invention, it is preferable that the endoscope-coupled part is provided with a frictional engagement part that frictionally engages with the larger-diameter part.

Additionally, in the second aspect of the invention, it is preferable that the endoscope is made of a high-friction member having a higher frictional coefficient at the coupling position than at other positions where the endoscope-coupled part is not coupled, and the endoscope-coupled part is made of a frictional engagement part that frictionally engages with the high-friction member.

An endoscope related to a third aspect of the invention is an endoscope that is guided into a body cavity via an overtube. The overtube includes an overtube body that passes through a body wall and is inserted into the body cavity, an endoscope insertion passage that is provided inside the overtube body and allows an endoscope for observing the inside of the body cavity to be inserted therethrough so as to be movable forward and backward, a treatment tool insertion passage that is provided inside the overtube body and allows a treatment tool for inspecting or treating an affected part within the body cavity to be inserted therethrough so as to be movable forward and backward, and an interlocking member that is configured to be movable forward and backward inside the overtube body, has an endoscope-coupled part to be coupled the endoscope inserted through the endoscope insertion passage and a treatment tool-coupled part to be coupled the treatment tool inserted through the treatment tool insertion passage, and has a dead zone where the forward and backward movement of either the endoscope or the treatment tool does not interlock with the movement of the other and a sensing zone where the forward and backward movement of either the endoscope or the treatment tool interlocks with the movement of the other. The overtube body includes a distal-end-side stopper that restricts the forward and backward movement of the interlocking member to a distal end side, and a base-end-side stopper that restricts the forward and backward movement of the interlocking member with respect to a base end side. In a state where the interlocking member has abutted against the base-end-side stopper and the forward and backward movement of the interlocking member to the base end side has been restricted, when a length from a coupling position of the endoscope, to which the endoscope-coupled part is coupled, to a distal end position of the overtube body in an axial direction of the overtube body is defined as L and a length from the coupling position to a distal end position of the endoscope is defined as Ls, the coupling position is set so as to satisfy the following formula.

$$Ls \geq L$$

Additionally, in the third aspect of the invention, it is preferable that the endoscope includes a smaller-diameter part that is arranged on the distal end side, and a larger-diameter part that is connected to the base end side of the smaller-diameter part, the endoscope-coupled part is configured to be non-engageable with the smaller-diameter part, and the endoscope-coupled part is configured to be engageable with the larger-diameter part.

Additionally, in the third aspect of the invention, it is preferable that the larger-diameter part frictionally engages with a frictional engagement part that is provided at the endoscope-coupled part.

Additionally, in the third aspect of the invention, it is preferable that the endoscope is made of a high-friction member having a higher frictional coefficient at the coupling position than at other positions where the endoscope-coupled part is not coupled, and the high-friction member frictionally engages with the frictional engagement part provided at the endoscope-coupled part.

According to the invention, the endoscope moves forward and backward with play with respect to the forward and backward movement of the treatment tool. Thus, when the treatment tool has been minutely displaced in the axial direction (when a forward and backward movement of a small amplitude has been performed), the size of an object to be observed can be prevented from fluctuating, a sense of perspective can be suitably maintained, and a stable observation image can be provided. Additionally, when the treatment tool has been largely displaced in the axial direction (when a forward and backward movement of a large amplitude has been performed), the range of an observation image obtained by the endoscope is changed in an interlocking manner. Thus, the size of an object to be observed changes according to the operation of the treatment tool, it is possible to simply obtain an image desired by a surgeon, and operability improves. Additionally, even if the endoscope moves forward and backward in an interlocking manner with the forward and backward movement of the treatment tool, the distal end of the endoscope does not enter the inside of the overtube. Thus, the visual field of the endoscope can always be secured, and it is possible to provide an optimum image without losing sight of an affected part during the endoscopic surgery.

BRIEF DESCRIPTION OF THE DRAWINGS

FIG. 21 is a sectional view illustrating the overtube in the endoscopic surgical device to which the present invention is applied.

FIG. 22 is a plan view illustrating an endoscope in the endoscopic surgical device to which the present invention is applied.

FIG. 23 is a sectional view illustrating a portion of the overtube immediately after a slider has been coupled to the endoscope insertion part of FIG. 22 in an enlarged manner.

FIG. 24 is a plan view illustrating another embodiment of the endoscope in the endoscopic surgical device to which the present invention is applied.

FIGS. 26A and 26B are views illustrating a situation in which the treatment tool insertion part is pushed into the affected part side within the body cavity from the hand side.

FIGS. 27A and 27B are views illustrating a situation in which the treatment tool insertion part is pushed into the affected part side within the body cavity from the hand side.

FIGS. 30A and 30B are views illustrating a situation in which the endoscope insertion part is extracted from and re-inserted into an overtube 300.

DESCRIPTION OF THE PREFERRED EMBODIMENTS

A preferred embodiment of the invention will be described below in detail according to the accompanying drawings. In addition, any drawing may illustrate main parts in an exaggerated manner for description, and may have dimensions different from actual dimensions. Additionally, in the following, characteristic parts of the invention will be described in detail after the basic configuration of an endoscope surgical device (endoscopic surgical device) is first described.

<Configuration of Endoscopic Surgical Device>

Figure 1:
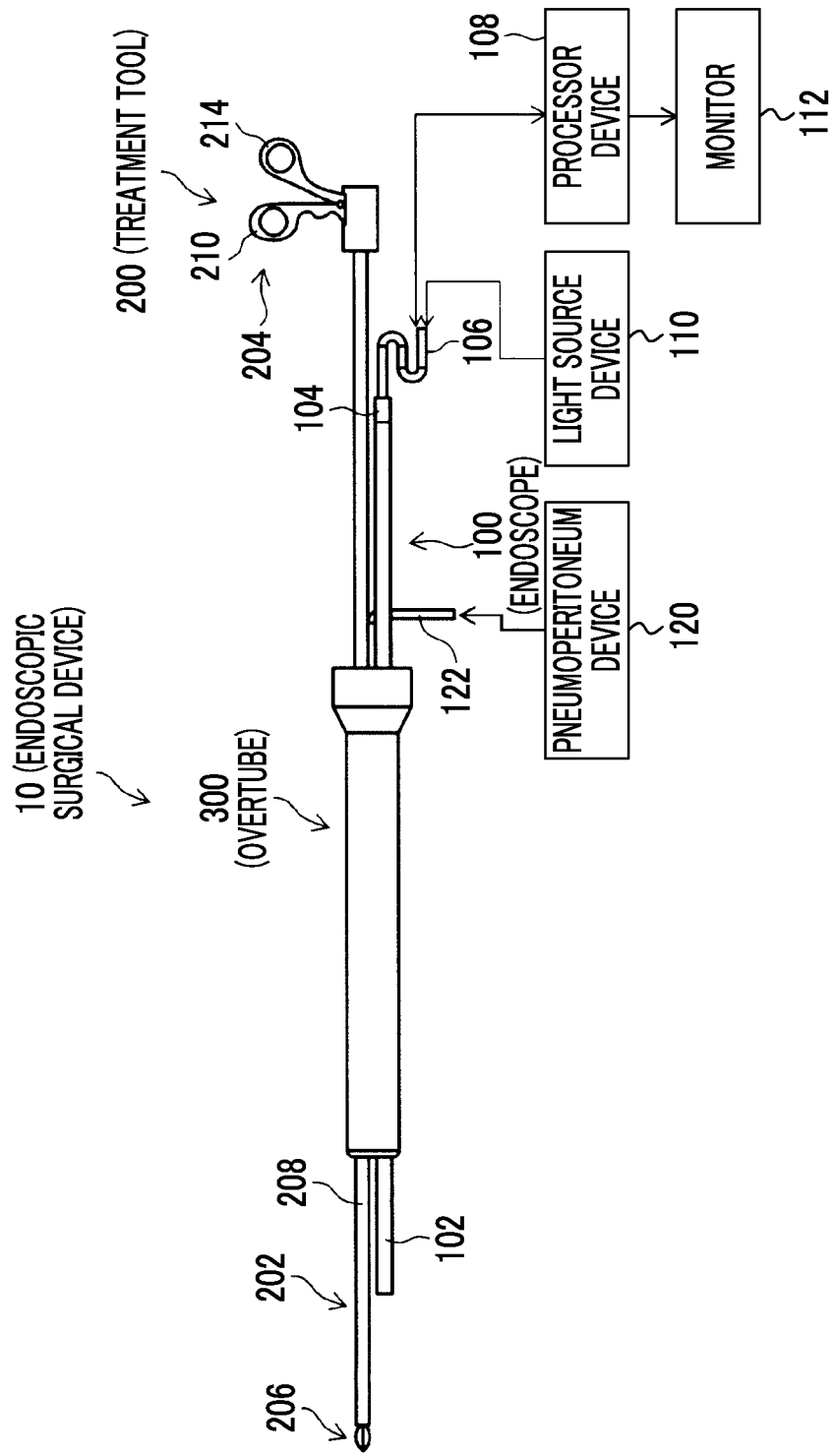
FIG. 1 is a schematic configuration diagram illustrating the basic configuration of an endoscopic surgical device.

FIG. 1 is a schematic configuration diagram illustrating the basic configuration of the endoscopic surgical device. As illustrated in FIG. 1, an endoscopic surgical device 10 includes an endoscope 100 that observes the inside of a patient's body cavity, a treatment tool 200 for inspecting or treating an affected part within the patient's body cavity, and an overtube 300 (guide member) that guides the endoscope 100 and the treatment tool 200 into the body cavity.

<Configuration of Endoscope>

The endoscope 100 includes an elongated insertion part (hereinafter referred to as "endoscope insertion part") 102 that is, for example, a hard endoscope, such as a laparoscope, and that is inserted into a body cavity, and an operating part 104 that is provided continuously with a base end side of the endoscope insertion part 102. A universal cable 106 is connected to the operating part 104, and each of a processor device 108 and a light source device 110 is detachably connected to a distal end part of the universal cable 106 via a connector (not illustrated). Additionally, the processor device 108 is connected to a monitor 112 via a cable.

Figure 2:
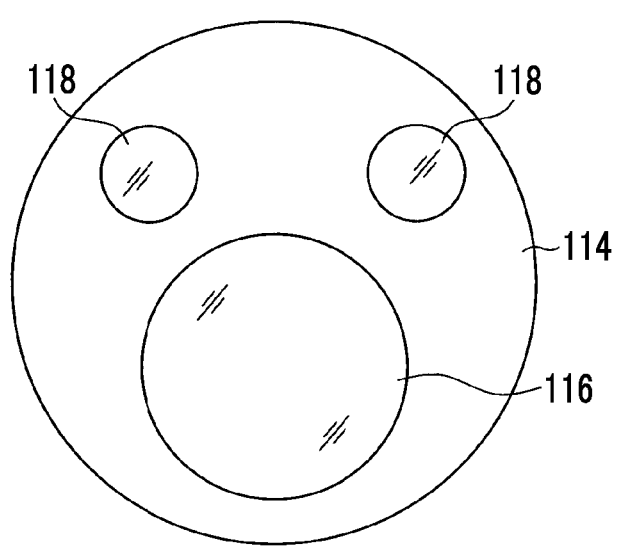
FIG. 2 is a plan view illustrating a distal end surface of an endoscope insertion part.

As illustrated in FIG. 2, a distal end surface 114 of the endoscope insertion part 102 is provided with an observation window 116 and illumination windows 118 and 118.

An objective lens of an observation optical system, and image pick-up elements, such as a charge-coupled device (CCD) and a complementary metal-oxide semiconductor (CMOS), which are arranged at an image formation position of the objective lens, are disposed behind the observation window 116. A signal cable (not illustrated) is connected to a substrate that supports the image pick-up element. The signal cable is inserted through the endoscope insertion part 102, the operating part 104, and the universal cable 106, and the like of FIG. 1, is provided to extend up to the connector (not illustrated), and is connected to the processor device 108. An observation image picked up by the observation window 116 is formed on a light-receiving surface of the image pick-up element, and is converted into electrical signals (image pick-up signals), and the electrical signals are output to the processor device 108 via the signal cable and are converted into video signals. Then, the video signals are output to the monitor 112 connected to the processor device 108, and the observation image (endoscope image) is displayed on a screen of the monitor 112.

An exit end of a light guide (not illustrated) is disposed behind the illumination windows 118 and 118 of FIG. 2. The light guide is inserted through the endoscope insertion part 102, the operating part 104, and the universal cable 106 of FIG. 1 and has an incident end disposed within the connector (not illustrated). Therefore, by coupling the connector to the light source device 110, the illumination light radiated from the light source device 110 is transmitted to the illumination windows 118 and 118 via the light guide, and is radiated forward from the illumination windows 118 and 118. In addition, in FIG. 2, the two illumination windows 118 and 118 are disposed on the distal end surface 114 of the endoscope insertion part 102. However, the number of the illumination windows 118 is not limited, and the number thereof may be one or three or more.

<Configuration of Treatment Tool>

As illustrated in FIG. 1, the treatment tool 200 consists of, for example, forceps, and includes an elongated insertion part (hereinafter referred to as a "treatment tool insertion part") 202 that is inserted into a body cavity, an operating part 204 that is provided on the base end side of the treatment tool insertion part 202 and is gripped by a surgeon, and a treatment part 206 that is provided on a distal end side of the treatment tool insertion part 202 and is operable by the operation of the operating part 204.

The treatment tool insertion part 202 is provided with a tubular sheath 208, and an operating shaft (not illustrated) that is inserted into the sheath 208 so as to be movable in the direction of an axial center. Moreover, the operating part 204 is provided with a fixed handle 210, and a movable handle 214 that is rotatably coupled to the fixed handle 210 via a turning pin. A base end part of the operating shaft is coupled to the movable handle 214.

The treatment part 206 is provided with a pair of gripping members capable of being openable and closable. The gripping members are coupled to a distal end part of the operating shaft via a driving mechanism (not illustrated). With the rotational operation of the movable handle 214 of the operating part 204, the gripping members of the treatment part 206 are opened and closed via the operating shaft and the driving mechanism.

In addition, the treatment tool 200 is not limited to the forceps, and may be, for example, other treatment tools, such as a laser probe, a suture device, an electric scalpel, a needle holder, and an ultrasonic aspirator.

<Configuration of Overtube>

Figure 3:
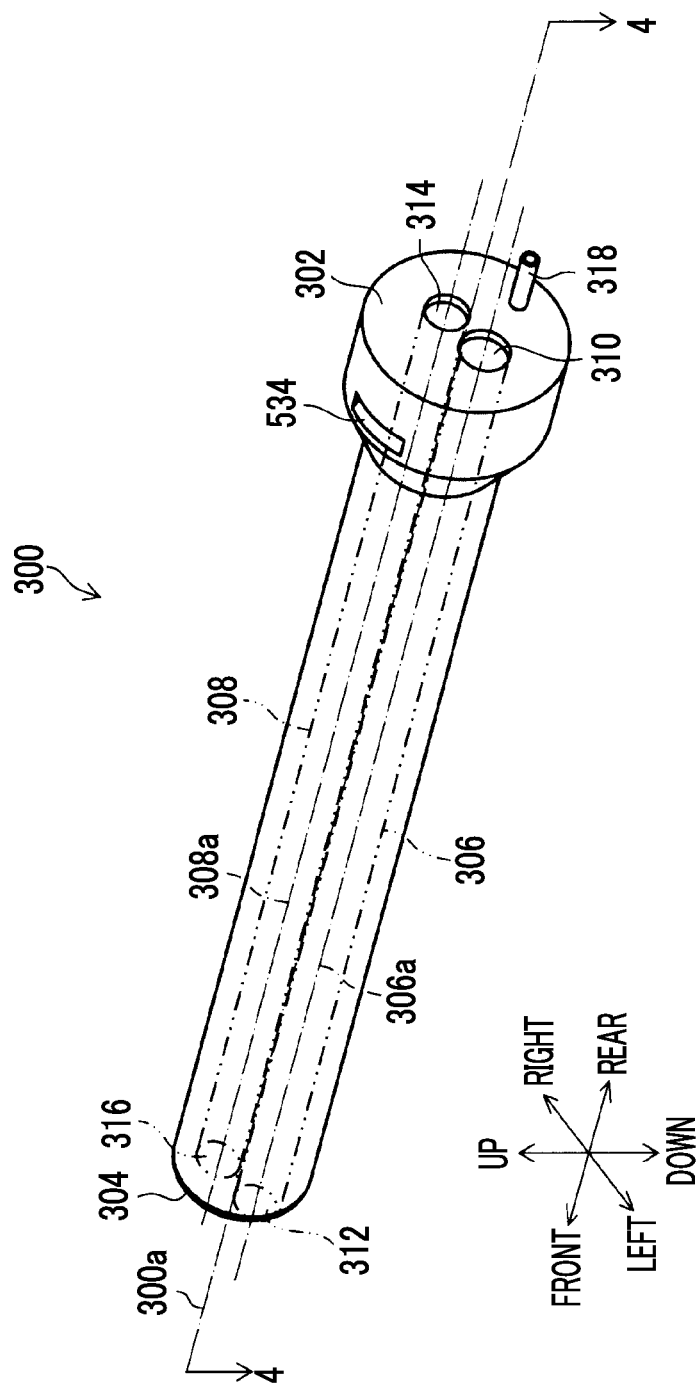
FIG. 3 is an external appearance perspective view illustrating an overtube from the rear upper left.

FIG. 3 is an external appearance perspective view illustrating the overtube 300 from the rear upper left.

As illustrated in this drawing, the overtube 300 has an endoscope insertion passage 306 through which the endoscope insertion part 102 of the endoscope 100 is inserted so as to be movable forward and backward, and a treatment tool insertion passage 308 through which the treatment tool insertion part 202 of the treatment tool 200 is inserted so as to be movable forward and backward.

The endoscope insertion passage 306 has a diameter such that at least the endoscope insertion part 102 is capable of being inserted therethrough, using an endoscope insertion axis 306a, which is parallel to a reference axis 300a (longitudinal axis) indicating a central axis of the entire overtube 300, as a central axis, and indicates a space portion within the overtube 300 that penetrates from a base end surface 302 of the overtube 300 to a distal end surface 304 thereof. The endoscope insertion axis 306a is equivalent to the position of the axis (central axis) of the endoscope insertion part 102 that is inserted through the endoscope insertion passage 306.

The base end surface 302 is provided with an endoscope insertion opening 310 for allowing the endoscope insertion part 102 to be inserted into the endoscope insertion passage 306 therethrough, and the distal end surface 304 is provided with an endoscope delivery opening 312 for allowing the endoscope insertion part 102 inserted into the endoscope insertion passage 306 to be delivered to the outside therethrough.

The treatment tool insertion passage 308 has a diameter such that at least the treatment tool insertion part 202 is capable of being inserted therethrough, using a treatment tool insertion axis 308a parallel to the reference axis 300a as a central axis, and indicates a space portion within the overtube 300 that penetrates from the base end surface 302 of the overtube 300 to the distal end surface 304. The treatment tool insertion axis 308a is equivalent to the position of the axis (central axis) of the treatment tool insertion part 202 that is inserted through the treatment tool insertion passage 308.

The base end surface 302 is provided with a treatment tool insertion opening 314 for allowing the treatment tool insertion part 202 to be inserted into the treatment tool insertion passage 308 therethrough, and the distal end surface 304 is provided with a treatment tool delivery opening 316 for allowing the treatment tool insertion part 202 inserted into the treatment tool insertion passage 308 to be delivered to the outside therethrough.

Additionally, the overtube 300 has an air supply connector 318 (fluid-supplying connector) on the base end surface 302. The air supply connector 318 is provided at the end part of an air supply pipe line that communicates with the endoscope insertion passage 306 and the treatment tool insertion passage 308 inside the overtube 300.

One end part of an air supply tube 122 (tube member) illustrated in FIG. 1 is connected to the air supply connector 318, and the other end part of the air supply tube 122 is connected to a pneumoperitoneum device 120. Therefore, if pneumoperitoneum gas (gas for pneumoperitoneum), such as carbon dioxide gas, is supplied from the pneumoperitoneum device 120 to the air supply tube 122, the pneumoperitoneum gas is sent from the air supply connector 318 to the inside of the overtube 300, and is delivered from the endoscope delivery opening 312 and the treatment tool delivery opening 316 of the distal end surface 304 through the inside of the overtube 300 to the outside of the overtube 300.

In addition, regarding the position and orientation of a space where the overtube 300 has been arranged, terms called front, rear, left, right, up, and down are used with the orientation from the base end surface 302 in a direction along the reference axis 300a to the distal end surface 304 defined as the front and with the orientation from the reference axis 300a to the endoscope insertion axis 306a defined as the left.

(Internal Structure of Overtube)

Figure 4:
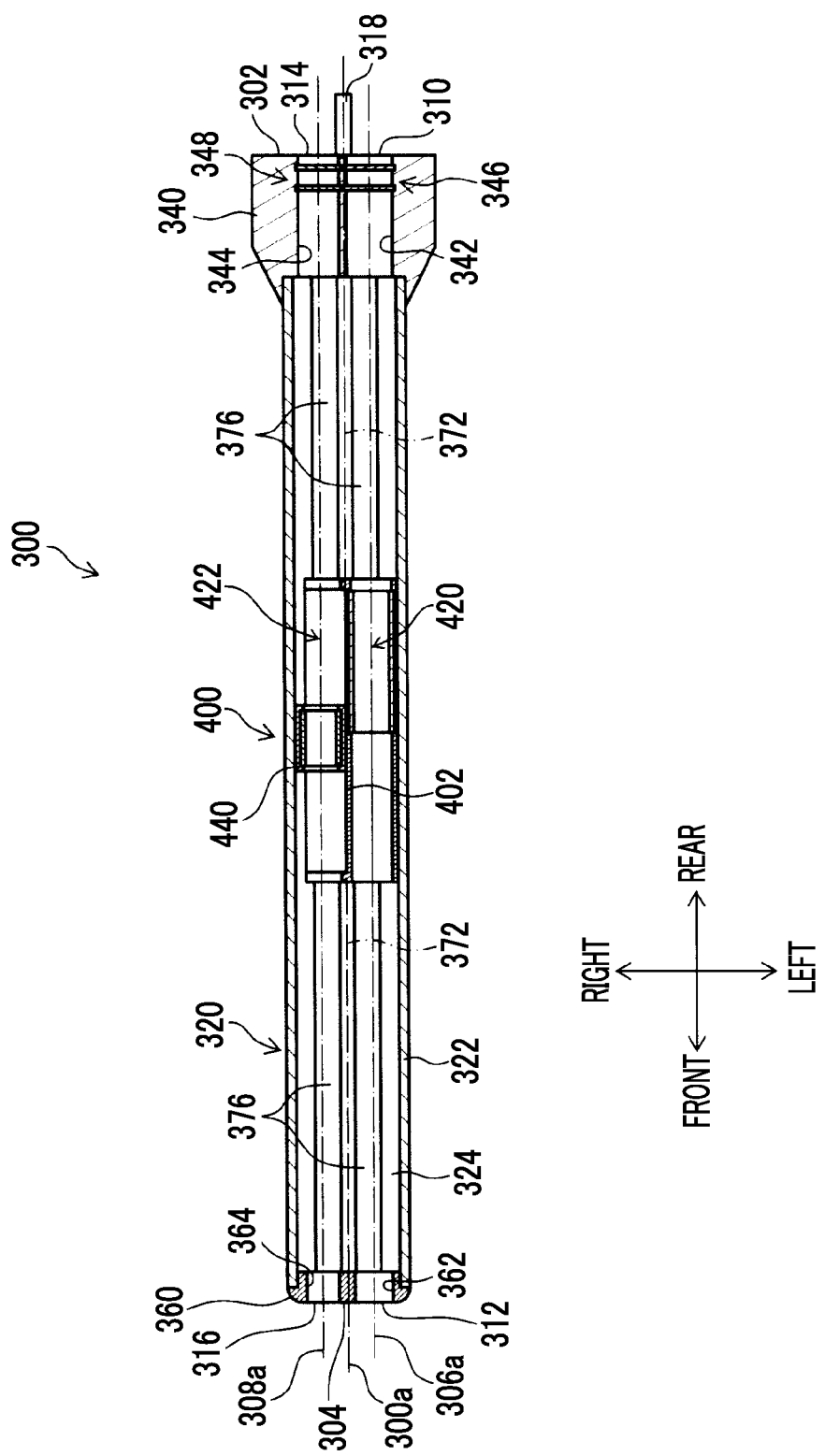
FIG. 4 is a sectional view, as seen from arrow 4-4 of FIG. 3, illustrating the internal structure of the overtube.

The specific configuration of the overtube 300 will be described. FIG. 4 is a sectional view (a sectional view as seen arrow 4-4 of FIG. 3) illustrating the internal structure of the overtube 300, and illustrates a section cut in a plane that includes the reference axis 300a and orthogonal to an upward-downward direction. In the present specification, when a drawing is simply called a sectional view, the drawing illustrates a sectional view cut by the same plane as FIG. 4.

As illustrated in this drawing, the overtube 300 has an overtube body 320 that occupies substantially the entire area in a forward-rearward direction, a base end cap 340 (base-end-side stopper) that is arranged at a rear part of the overtube 300, a distal end cap 360 (distal-end-side stopper) that is arranged at a distal end part, and a slider 400 (interlocking member) that is arranged inside the overtube 300. In addition, the base end cap 340 and the distal end cap 360 are some of the constituent elements of the overtube body of the invention, and may be formed separately from or formed integrally with the overtube body 320.

(Description of Overtube Body)

The overtube body 320 is formed in an elongated cylindrical shape having the reference axis 300a as a central axis using hard resin, metal, or the like, and has an outer wall 322 that surrounds an outer periphery, and a lumen 324 that penetrates from a base end of the overtube body 320 to a distal end thereof.

The lumen 324 has the endoscope insertion axis 306a and the treatment tool insertion axis 308a inserted therethrough, and is provided with a space that serves as the endoscope insertion passage 306 and the treatment tool insertion passage 308.

Additionally, the lumen 324 serves as the air supply pipe line through which the pneumoperitoneum gas sent in from the air supply connector 318 passes.

The base end cap 340 is attached to the base end of the overtube body 320, and is formed in a columnar shape made to have a larger diameter than the external diameter of the overtube body 320, using hard resin, metal, or the like. The base end cap 340 has a flat rear end surface serving as the base end surface 302 of the overtube 300 on the rear side thereof, and has through-holes 342 and 344 that penetrate from the base end surface 302 to the lumen 324 of the overtube body 320.

The through-hole 342 has a central axis arranged coaxially with the endoscope insertion axis 306a, and forms a portion of the endoscope insertion passage 306. An opening of the through-hole 342 in the base end surface 302 is equivalent to the above-described endoscope insertion opening 310.

The through-hole 344 has a central axis arranged coaxially with the treatment tool insertion axis 308a, and forms a portion of the treatment tool insertion passage 308. An opening of the through-hole 344 in the base end surface 302 is equivalent to the above-described treatment tool insertion opening 314.

Valve members 346 and 348 (a first valve member 346, a second valve member 348) are respectively arranged in the through-hole 342 and the through-hole 344. Although the detailed description of the valve members 346 and 348 is omitted, the valve members have, for example, slits that open only when being inserted through the endoscope insertion part 102 and the treatment tool insertion part 202 and that come into close contact with outer peripheral surfaces (side surfaces) of the endoscope insertion part 102 and the treatment tool insertion part 202 without a substantial gap. This secures the airtightness of spaces closer to the distal end side than the valve members 346 and 348, and reduces the leakage or the like of the pneumoperitoneum gas injected into the body cavity to the outside of the body.

In addition, the valve members 346 and 348 are not limited to those with the specific configuration, and valve members with widely-known arbitrary configurations can be used. Although FIG. 4 illustrates a configuration in which the two valve members are respectively arranged in the through-hole 342 and the through-hole 344, a configuration in which one valve member or three or more valve members are arranged may be adopted.

(Description of Air Supply Connector)

Figure 5:
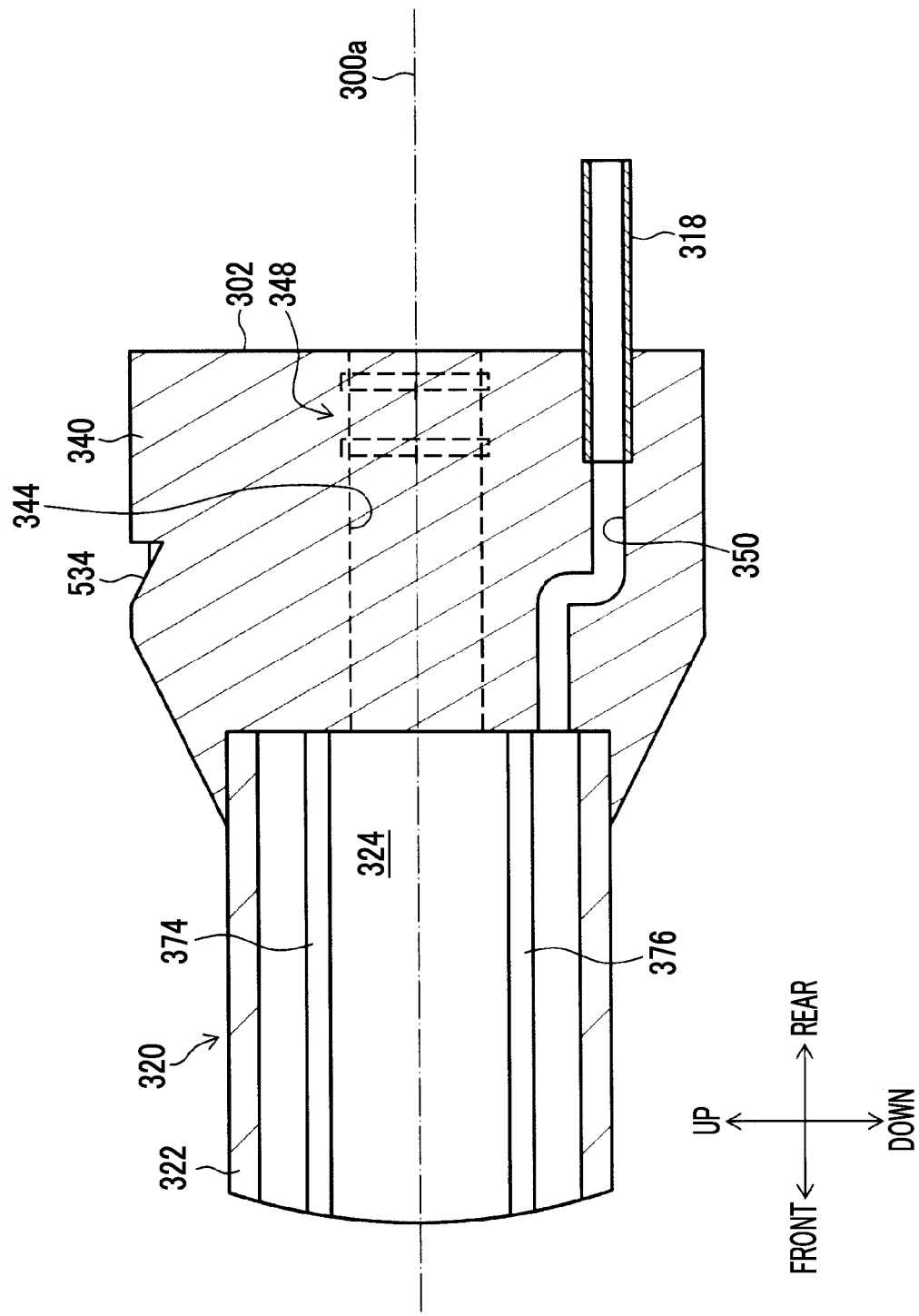
FIG. 5 is a sectional view of the periphery of a base end cap cut in a plane orthogonal to a paper surface of FIG. 4.

Additionally, FIG. 5 is a sectional view of the periphery of the base end cap 340 when the overtube 300 is cut in a plane that includes the reference axis 300a and is orthogonal to the paper surface of FIG. 4. As illustrated in this drawing, the base end cap 340 has a through-hole 350 that penetrates from the base end surface 302 to the lumen 324 of the overtube body 320.

The through-hole 350 is a portion of the air supply pipe line that allows the pneumoperitoneum gas to flow therethrough, and has a rear end part formed at a position below the reference axis 300a. The rear end part is provided with the above-described air supply connector 318 to which the air supply tube 122 (refer to FIG. 1) from the pneumoperitoneum device 120 is connected.

The air supply connector 318 is formed in an elongated cylindrical shape, and has a part buried and fixed inside the through-hole 350. Accordingly, at a position below the reference axis 300a in the base end surface 302, the axis (central axis) of the air supply connector 318 is arranged so as to be substantially orthogonal to the base end surface 302 (arranged parallel to the reference axis 300a), and the air supply connector 318 is provided to protrude rearward from the base end surface 302.

The air supply tube 122 is connected to the air supply connector 318 by fitting the air supply tube 122 to the outer periphery of the air supply connector 318. Then, if the pneumoperitoneum gas is delivered from the pneumoperitoneum device 120 to the air supply tube 122, the pneumoperitoneum gas is sent into the lumen 324 of the overtube body 320 from the air supply connector 318.

(Merits Based on Arrangement of Air Supply Connector on Base End Surface)

Here, in an overtube that guides one medical instrument into a body cavity, it is general that the air supply connector is provided not on a base end surface of the overtube but on a side surface thereof.

This is because the air supply connector may interfere with an inner needle supposing that the air supply connector is provided on the base end surface, and because the overtube can be rotated around the axis so as to prevent the interference of the air supply connector and the air supply tube with a body wall without influencing the position of the medical instrument inserted through the overtube even if the air supply connector is provided on the side surface.

On the other hand, in the overtube 300 of the present embodiment, if the overtube 300 is rotated around the axis, the position of the endoscope insertion part 102 and the treatment tool insertion part 202 changes. Therefore, a case where it is difficult to avoid any interference of the air supply connector 318 and the air supply tube 122 with the body wall while maintaining the positions of the endoscope insertion part 102 and the treatment tool insertion part 202 within the body cavity at positions desired by a surgeon may occur.

Thus, in the overtube 300 of the present embodiment, the interference of the air supply connector 318 and the air supply tube 122 with the body wall is prevented by arranging the air supply connector 318 on the base end surface 302 of the overtube 300, and the interference of the air supply tube with the inner needle is avoided by devising the configuration of the inner needle as will be described below.

In addition, the air supply pipe line within the air supply connector 318 and the overtube 300 may be provided in order to supply fluids other than the pneumoperitoneum gas into a body cavity.

The distal end cap 360 illustrated in FIG. 4 is attached to the distal end of the overtube body 320, and is formed of hard resin, metal, or the like. The distal end cap 360 has a front surface serving as the distal end surface 304 of the overtube 300 on a front side thereof, and has through-holes 362 and 364 that penetrate from the lumen 324 of the overtube body 320 to the distal end surface 304.

The through-hole 362 has a central axis arranged coaxially with the endoscope insertion axis 306a, and forms a portion of the endoscope insertion passage 306. An opening of the through-hole 362 in the distal end surface 304 is equivalent to the above-described endoscope delivery opening 312.

The through-hole 364 has a central axis arranged coaxially with the treatment tool insertion axis 308a, and forms a portion of the treatment tool insertion passage 308. An opening of the through-hole 364 in the distal end surface 304 is equivalent to the above-described treatment tool delivery opening 316.

Additionally, as described above, the pneumoperitoneum gas sent into the lumen 324 of the overtube body 320 via the air supply tube 122, the air supply connector 318 of the base end cap 340, and the through-hole 350 from the pneumoperitoneum device 120 is delivered to the outside (the inside of a body cavity) via the through-hole 362 and the through-hole 364.

Although the overtube body 320, the base end cap 340, and the distal end cap 360 above form the outer wall of the overtube 300, the outer wall of the overtube 300 may not necessarily be constituted of these separated members.

The air supply pipe line of the overtube body 320 through which the pneumoperitoneum gas passes may be a lumen that is provided separately from the lumen 324.

(Description of Slider)

Next, the slider 400 will be described.

The slider 400 illustrated in FIG. 4 is housed within the lumen 324 of the overtube body 320, and is supported so as to be movable forward and backward in the direction of the reference axis 300a.

The slider 400 is an interlocking member that is coupled to the endoscope insertion part 102 inserted through the endoscope insertion passage 306 and the treatment tool insertion part 202 inserted through the treatment tool insertion passage 308 and that has a dead zone where the forward and backward movement of either the endoscope insertion part or the treatment tool insertion part in the forward-rearward direction (axial direction) does not interlock with the movement of the other and a sensing zone where the forward and backward movement of either the endoscope insertion part or the treatment tool insertion part interlocks with the movement of the other.

That is, the endoscope insertion part 102 is adapted to interlock with the forward and backward movement of the treatment tool insertion part 202 in the axial direction with play.

Accordingly, when a surgeon has moved the treatment tool insertion part 202 forward and backward in the axial direction and when the axial displacement of the treatment tool insertion part 202 is large (when a forward and backward movement of a large amplitude has been performed), the endoscope insertion part 102 also moves in an interlocking manner forward, backward, upward, downward, rightward, and leftward. Thus, the visual field, orientation, and the like of the endoscope 100 can be changed as intended by a surgeon. Additionally, the visual field is always given to pick up an image of a treatment tool distal end, and consequently, an image that is optimal for treatment is automatically provided. When it is desired to check places other than the treatment part, the checking can be performed by moving forceps, and a surgeon can perform operations as desired. Therefore, an assistant (scopist) who operates the endoscope 100 apart from the surgeon can be made unnecessary, and a troublesome condition in which the surgeon should instruct an assistant about the visual field, orientation, and the like of the endoscope serially can be eliminated.

Additionally, when the axial displacement of the treatment tool insertion part 202 is small (when a forward and backward movement of a small amplitude has been performed), the endoscope insertion part 102 does not interlock. Therefore, the size of an object to be observed within an observation image can be prevented from fluctuating unnecessarily, a sense of perspective can be suitably maintained, and a stable observation image can be provided.

(Internal Structure of Slider)

The internal structure of the slider 400 will be described.

Figure 6:
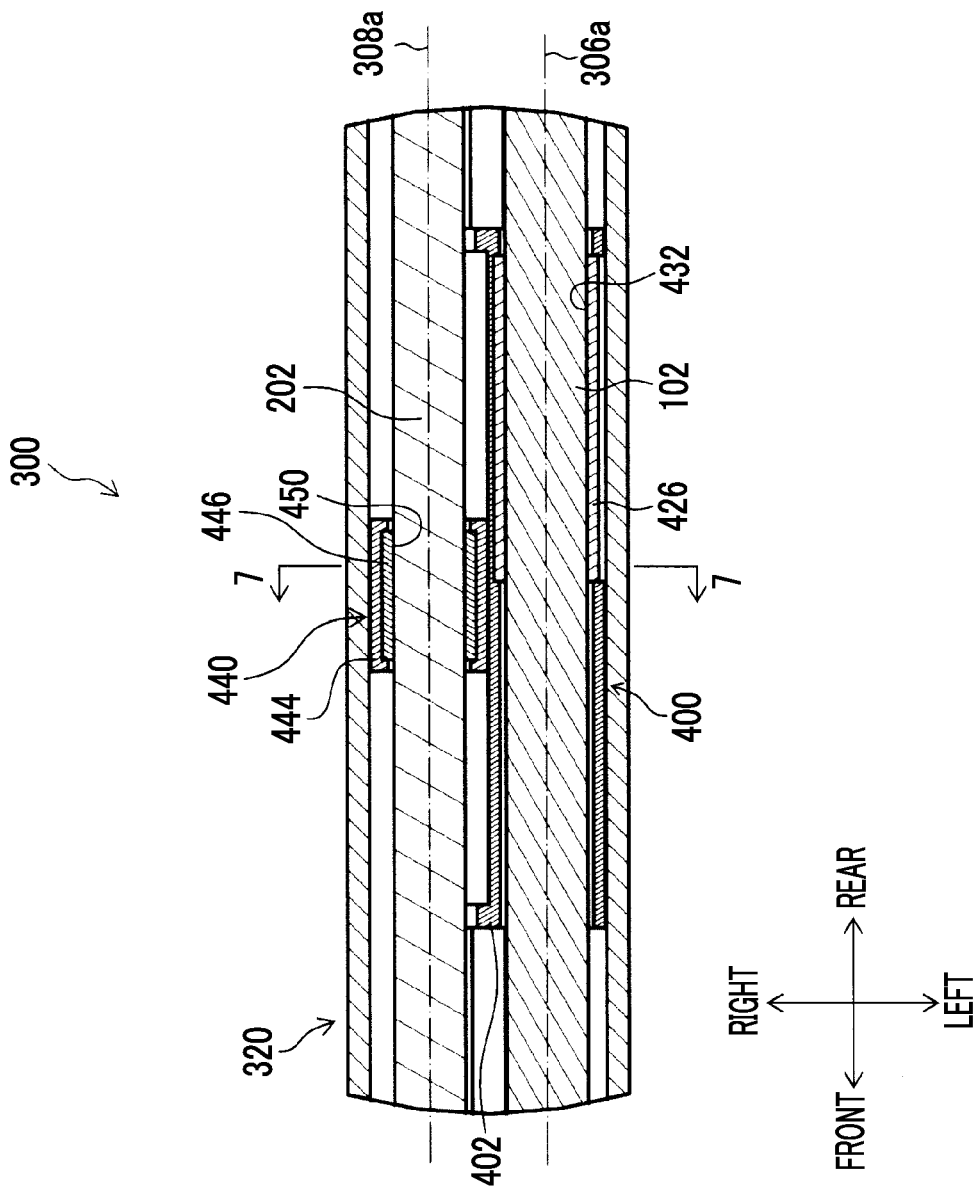
FIG. 6 is an enlarged sectional view illustrating a portion of FIG. 4 in an enlarged manner.

FIG. 6 is an enlarged sectional view illustrating a portion, in which the slider 400 is arranged in FIG. 4, in an enlarged manner, and illustrates a state where the endoscope insertion part 102 and the treatment tool insertion part 202 have been inserted through the endoscope insertion passage 306 and the treatment tool insertion passage 308, respectively.

Figure 7:
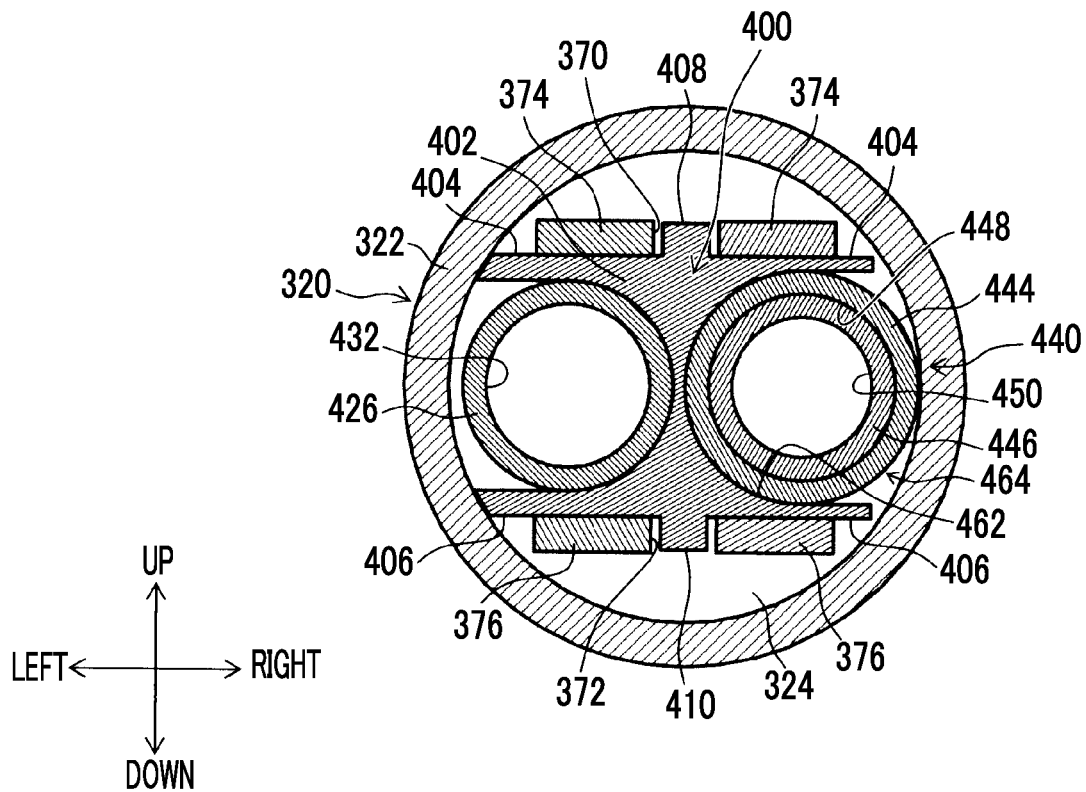
FIG. 7 is a sectional view as seen from arrow 7-7 in FIG. 6.

FIG. 7 is a sectional view as seen from arrow 7-7 in FIG. 6.

Figure 8:
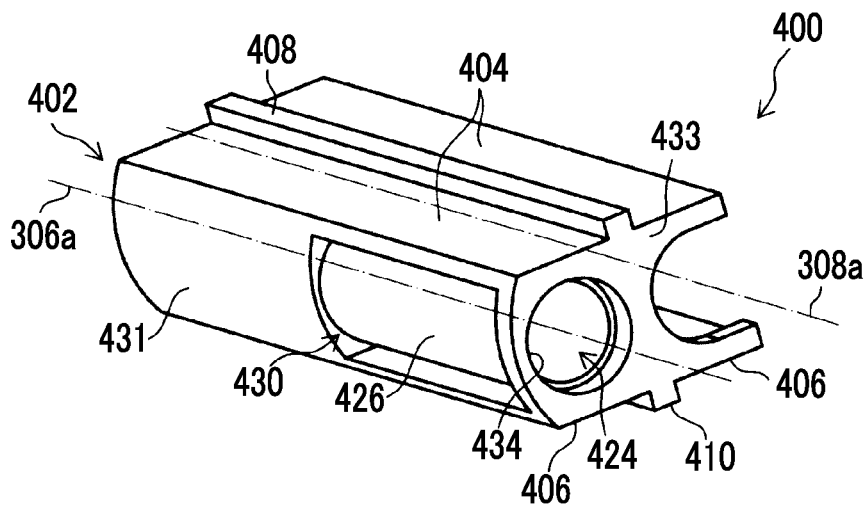
FIG. 8 is a perspective view illustrating a slider from the rear upper left.
Figure 9:
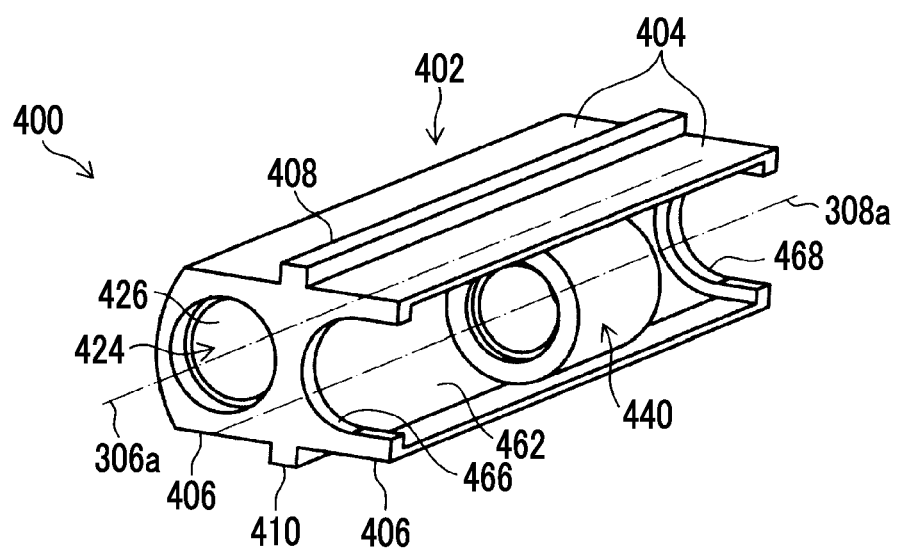
FIG. 9 is a perspective view illustrating the slider from the rear upper right.
Figure 10:
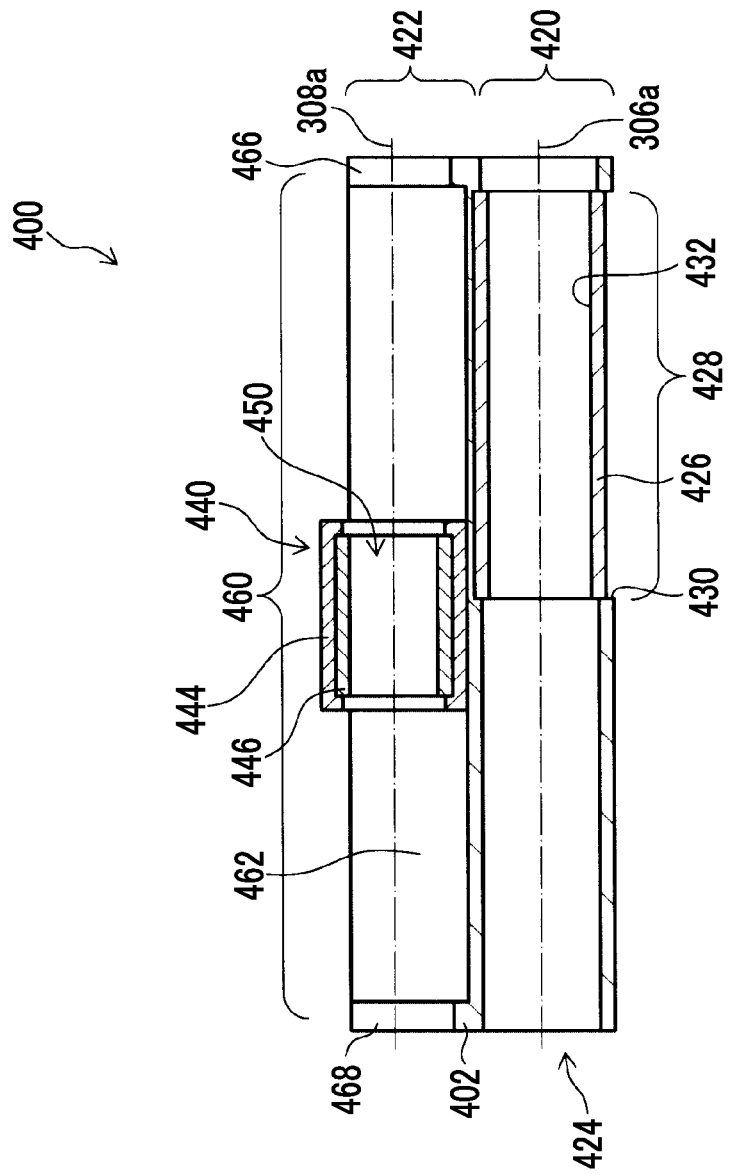
FIG. 10 is a sectional view of the slider.

Additionally, FIGS. 8 and 9 are respectively perspective views illustrating the slider 400 from the rear upper left and from the rear upper right and FIG. 10 is a sectional view of only the slider 400.

As illustrated in FIGS. 6 to 10, the slider 400 has a slider body 402 (slider member) that holds components of the slider 400. The slider body 402, as illustrated in FIGS. 7 to 9, has a flat upper surface 404 and a flat lower surface 406, and has protruding strips 408 and 410, respectively, on the upper surface 404 and the lower surface 406.

The protruding strips 408 and 410 respectively protrude in the upward-downward direction at substantially central parts of the upper surface 404 and the lower surface 406 in a leftward-rightward direction, extend in the direction (forward-rearward direction) of the reference axis 300a within the lumen 324 of the overtube body 320, and are fitted into guide grooves 370 and 372 provided in an upper part and a lower part within the lumen 324 of the overtube body 320 as illustrated in FIG. 7.

The guide grooves 370 and 372 are respectively formed by gaps between a pair of left and right guide plates 374 and 374 and a pair of left and right the guide plates 376 and 376 that are arranged at the upper part and the lower part within the lumen 324.

The guide plates 376 and 376 arranged at the lower part within the lumen 324 are illustrated in FIG. 4. As illustrated in this drawing, the guide plates 374 and 374 and the guide plates 376 and 376 are respectively formed in the shape of a long plate, and are installed along the direction of the reference axis 300a by being laid between the base end cap 340 and the distal end cap 360.

Accordingly, the guide grooves 370 and 372 are respectively arranged along the direction of the reference axis 300a from the base end cap 340 to the distal end cap 360 within the lumen 324.

As illustrated in FIG. 7, in a state where the slider 400 is housed and arranged within the lumen 324, the protruding strips 408 and 410 are respectively fitted into the guide grooves 370 and 372, and the upper surface 404 and the lower surface 406 respectively contact or approach the guide plates 374 and 374 and the guide plates 376 and 376. Accordingly, the slider 400 (slider body 402) is supported so as to be movable forward and backward in the forward-rearward direction within the lumen 324, and is supported in a state where the movement of the slider in the upward-downward direction and in the leftward-rightward direction and the rotation of the slider in all directions are restricted (a state where the rotation of the slider around at least the reference axis 300a is impossible).

In addition, the guide grooves 370 and 372 may not be formed by the guide plates 374 and 374 and the guide plates 376 and 376 arranged within the lumen 324 of the overtube body 320, and may be formed in the outer wall 322 of the overtube body 320 or may be formed by other configurations.

Additionally, a range (movable range) in which the slider 400 (slider body 402) moves forward and backward in the forward-rearward direction with respect to the overtube body 320 is a range having a position where the slider 400 abuts against the base end cap 340 as a rear end (a position closest to the base end) and having a position where the slider abuts against the distal end cap 360 as a front end (a position closest to the distal end). However, the rear end and the front end of the movable range of the slider 400 may not be restricted by the base end cap 340 and the distal end cap 360.

Additionally, the slider 400, as illustrated in FIG. 10, has an endoscope-coupled part 420 that is coupled (engaged) with the endoscope insertion part 102, and a treatment tool-coupled part 422 that is coupled (engaged) with the treatment tool insertion part 202.

(Description of Endoscope-Coupled Part)

The endoscope-coupled part 420 is provided on the left side of the slider body 402, and includes a through-hole 424 in which a space serving as the endoscope insertion passage 306 is secured within the lumen 324 of the overtube body 320 and through which, as illustrated in FIG. 6, the endoscope insertion part 102 is inserted, and a pressure-contact member 426 that is brought into pressure contact with the outer peripheral surface (side surface) of the endoscope insertion part 102 inserted through the endoscope insertion passage 306.

The through-hole 424 is formed to penetrate from a rear end of the slider body 402 to a front end thereof, and has a larger diameter than the external diameter of at least the endoscope insertion part 102. A central axis of the through-hole 424 is arranged coaxially with the endoscope insertion axis 306a within the lumen 324.

A pressure-contact member attachment part 428 for attaching the pressure-contact member 426 is provided on the rear end side of the through-hole 424.

The pressure-contact member attachment part 428 has an internal diameter that is made larger than other position ranges of the through-hole 424, and has formed therein an opening 430 (refer to FIG. 8) that penetrates up to an outer surface (left side surface 431) of the slider body 402 in a partial range thereof (a left side surface of the slider 400) in the circumferential direction. The pressure-contact member 426 is fitted into the through-hole 424 from the opening 430, and the pressure-contact member 426 is fixed to the slider body 402 in the pressure-contact member attachment part 428.

The pressure-contact member 426, as illustrated in FIG. 7, is annularly formed of an elastic material, such as elastic rubber or a spring, and a central axis of a through-hole 432 thereof is arranged coaxially with the endoscope insertion axis 306a.

Accordingly, when the endoscope insertion part 102 is inserted through the endoscope insertion passage 306, as illustrated in FIG. 6, the endoscope insertion part 102 is inserted through the through-hole 432 of the pressure-contact member 426.

In addition, the position of an outer peripheral surface of the pressure-contact member 426 in the opening 430 of the pressure-contact member attachment part 428 substantially coincides with the position of the left side surface 431 of the slider body 402 around the opening 430. That is, the opening 430 of the pressure-contact member attachment part 428 provides a space for arranging the pressure-contact member 426, and as compared to a configuration in which the pressure-contact member 426 is completely housed inside the slider body 402, the slider body 402 is miniaturized, and the external diameter of the overtube body 320 is also made smaller along with this miniaturization. However, a configuration in which the pressure-contact member 426 is completely housed inside the slider body 402 may be adopted.

Additionally, the internal diameter (the diameter of the through-hole 432) of the pressure-contact member 426 is slightly smaller than the external diameter of the endoscope insertion part 102.

Therefore, when the endoscope insertion part 102 is inserted through the through-hole 432 of the pressure-contact member 426, the through-hole 432 is pushed and widened and the pressure-contact member 426 is deformed. An elastic force is generated in the pressure-contact member 426 due to this deformation, and the pressure-contact member 426 is brought into pressure contact (engaged) with the endoscope insertion part 102 inserted through the through-hole 432.

Therefore, a frictional force acts on the relative movement between the endoscope insertion part 102 and the pressure-contact member 426. Then, unless a larger external force than the frictional force is applied between the endoscope insertion part 102 and the pressure-contact member 426, the relative movement does not occur between the endoscope insertion part 102 and the pressure-contact member 426, and the endoscope insertion part 102 and the slider 400 (slider body 402) are brought into a state where they are coupled (engaged) in an interlockable manner via the pressure-contact member 426.

Accordingly, the slider 400 (slider body 402) also integrally moves forward and backward in an interlocking manner with the forward and backward movement of the endoscope insertion part 102 in the forward-rearward direction (axial direction).

In addition, since the coupling here is based on the elastic force of the pressure-contact member 426, the engagement position (a position where the slider 400 is engaged in the endoscope insertion part 102) of the endoscope insertion part 102 coupled to the slider 400 (slider body 402) can be arbitrarily adjusted.

(Description of Treatment Tool-Coupled Part)

The treatment tool-coupled part 422, as illustrated in FIG. 10 is provided on the right side of the slider body 402, and includes a sleeve 440 (sleeve member) that is coupled to the treatment tool insertion part 202, and a guide part 460 that guides the sleeve 440 so as to be movable forward and backward in the direction (forward-rearward direction) of the treatment tool insertion axis 308a.

The sleeve 440 is housed in a sleeve housing space 464 of the guide part 460 to be described below in detail, is supported so as to be movable forward and backward in the forward-rearward direction, and as illustrated in FIG. 7, includes a sleeve body (frame body) 444 that surrounds the outside of the sleeve, and a pressure-contact member 446 that is arranged inside the sleeve.

The sleeve body 444 is formed in a cylindrical shape, and has a through-hole 448 with a larger diameter than the external diameter of at least the treatment tool insertion part 202. The central axis of the through-hole 448 is arranged coaxially with the treatment tool insertion axis 308a within the lumen 324 of the overtube body 320, and secures a space for the treatment tool insertion passage 308.

The pressure-contact member 446 is annularly formed of an elastic material, such as elastic rubber or a spring, and is fitted into the through-hole 448 of the sleeve body 444 and fixed to the sleeve body 444. A central axis of a through-hole 450 of the pressure-contact member 446 is arranged coaxially with the treatment tool insertion axis 308a within the lumen 324 of the overtube body 320.

Therefore, when the treatment tool insertion part 202 is inserted through the treatment tool insertion passage 308, as illustrated in FIG. 6, the treatment tool insertion part 202 is inserted through the through-hole 450 of the pressure-contact member 446.

Additionally, the internal diameter (the diameter of the through-hole 450) of the pressure-contact member 446 is slightly smaller than the external diameter of the treatment tool insertion part 202.

Therefore, when the treatment tool insertion part 202 is inserted through the through-hole 450 of the pressure-contact member 446, the through-hole 450 is pushed and widened and the pressure-contact member 446 is deformed. An elastic force is generated in the pressure-contact member 446 due to this deformation, and the pressure-contact member 446 is brought into pressure contact (engaged) with the treatment tool insertion part 202 inserted through the through-hole 450.

Therefore, a frictional force acts on the relative movement between the treatment tool insertion part 202 and the pressure-contact member 446. Then, unless a larger external force than the frictional force is applied between the treatment tool insertion part 202 and the pressure-contact member 446, the relative movement does not occur between the treatment tool insertion part 202 and the pressure-contact member 446, and the treatment tool insertion part 202 and the sleeve 440 are brought into a state where they are coupled (engaged) in an interlockable manner via the pressure-contact member 446.

Accordingly, the sleeve 440 also integrally moves forward and backward in an interlocking manner with the forward and backward movement of the treatment tool insertion part 202 in the forward-rearward direction (axial direction).

Additionally, the sleeve 440 also rotates with respect to the slider body 402 in an interlocking manner with the rotation around the axis of the treatment tool insertion part 202.

In addition, since the coupling between the treatment tool insertion part 202 and the sleeve 440 herein is based on the elastic force of the pressure-contact member 446, the engagement position (a position where the sleeve 440 is engaged in the treatment tool insertion part 202) of the treatment tool insertion part 202 coupled to the sleeve 440 can be arbitrarily adjusted.

Additionally, a region where the endoscope insertion part 102 is fixed to the endoscope-coupled part 420 of the slider 400 is referred to as an endoscope fixed region, and a region where the treatment tool insertion part 202 is fixed to the treatment tool-coupled part 422 of the slider 400 is referred to as a treatment tool fixed region. In the present form, the endoscope fixed region is equivalent to a region of an inner peripheral surface of the pressure-contact member 426 that is brought into pressure contact with the outer peripheral surface of the endoscope insertion part 102, and the treatment tool fixed region is equivalent to a region of an inner peripheral surface of the pressure-contact member 446 that is brought into pressure contact with the outer peripheral surface of the treatment tool insertion part 202. In this case, it is desirable that the endoscope fixed region is configured so as to become longer in the axial direction than the treatment tool fixed region.

Meanwhile, the guide part 460 of the treatment tool-coupled part 422, as illustrated in FIGS. 7 and 9, has a guide surface 462 that extends in the direction of the treatment tool insertion axis 308a (reference axis 300a) within the lumen 324 of the overtube body 320.

The guide surface 462 is curved in a U-shape with an opening directed rightward in a section orthogonal to the reference axis 300a, and as illustrated in FIG. 7, an inner peripheral surface of the overtube body 320 (outer wall 322) is arranged so as to face the opening of the guide surface 462, within the lumen 324 of the overtube body 320.

Accordingly, a space surrounded by the guide surface 462 and the inner peripheral surface of the overtube body 320 is formed as the sleeve housing space 464 of the guide part 460.

The sleeve housing space 464 is formed at a position where the treatment tool insertion axis 308a is inserted therethrough, and extends along the treatment tool insertion axis 308a.

The sleeve 440 is housed and arranged in the sleeve housing space 464 as described above, and a central axis of the sleeve 440 is arranged coaxially with the treatment tool insertion axis 308a.

In the sleeve housing space 464, an outer peripheral surface of the sleeve 440 comes in contact with or approaches the guide surface 462 and the inner peripheral surface of the overtube body 320.

Accordingly, in the sleeve housing space 464, the sleeve 440 is supported so as to be movable in the forward-rearward direction and rotatable around the axis, and is supported in a state where the movement of the sleeve in the upward-downward direction and in the leftward-rightward direction is restricted.

Additionally, the guide part 460 (slider body 402), as illustrated in FIGS. 9 and 10, has end edge parts 466 and 468, which are formed to protrude in a direction orthogonal to the guide surface 462 along an end edge of the guide surface 462, respectively, on the base end side and the distal end side thereof.

The end edge parts 466 and 468 abut against the end part of the sleeve 440 to restrict the movement of the sleeve 440, when the sleeve 440 arranged in the sleeve housing space 464 moves forward and backward in the forward-rearward direction.

Therefore, a range (movable range) where the sleeve 440 moves forward and backward in the forward-rearward direction with respect to the slider body 402 is limited with a position where the sleeve abuts against the end edge part 466 being defined as a rear end and a position where the sleeve abuts against the end edge part 468 being defined as a front end. However, the rear end and the front end of the movable range of the sleeve 440 may not be restricted by the end edge part 466 and the end edge part 468.

In addition, in the present embodiment, the sleeve housing space 464 of the guide part 460 is formed by the guide surface 462 of the slider body 402 and the inner peripheral surface of the overtube body 320. Therefore, as compared to a configuration in which the sleeve housing space 464 is formed only by the slider body 402 and the sleeve 440 is completely housed inside the slider body 402, the slider body 402 is miniaturized, and the external diameter of the overtube body 320 is also made smaller along with this miniaturization. However, a configuration in which the sleeve 440 is completely housed inside the slider body 402 may be adopted.

(Action of Slider when Endoscope and Treatment Tool are Coupled)

According to the slider 400 configured as described above, the endoscope insertion part 102 inserted through the endoscope insertion passage 306 of the overtube 300 and the slider body 402 are coupled, and the treatment tool insertion part 202 inserted through the treatment tool insertion passage 308 of the overtube 300 and the sleeve 440 are coupled.

Figure 11:
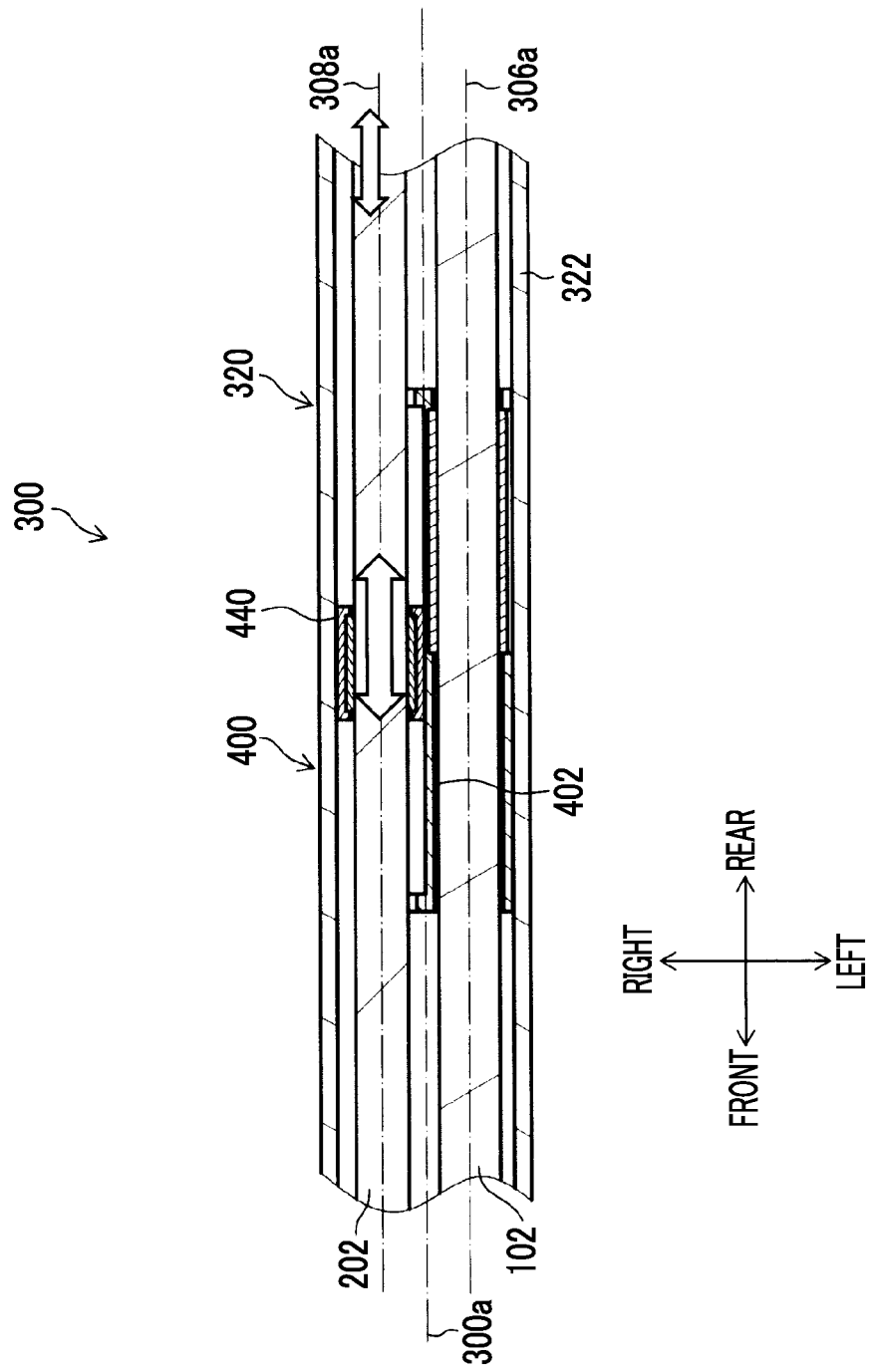
FIG. 11 is an explanatory view used for the description of the action of the slider.

As illustrated in FIG. 11, it is supposed that a surgeon performs a forward and backward movement for moving the treatment tool insertion part 202 forward and backward in the axial direction (forward-rearward direction) in a state where the sleeve 440 has not reached the rear end and the front end of the movable range thereof with respect to the slider body 402.

In this case, when the sleeve 440 has moved forward and backward within the movable range thereof with respect to the slider body 402, the slider body 402 does not move with respect to the forward and backward movement of the treatment tool insertion part 202. Therefore, the dead zone where the endoscope insertion part 102 does not interlock with the forward and backward movement of the treatment tool insertion part 202 is present.

Figure 12:
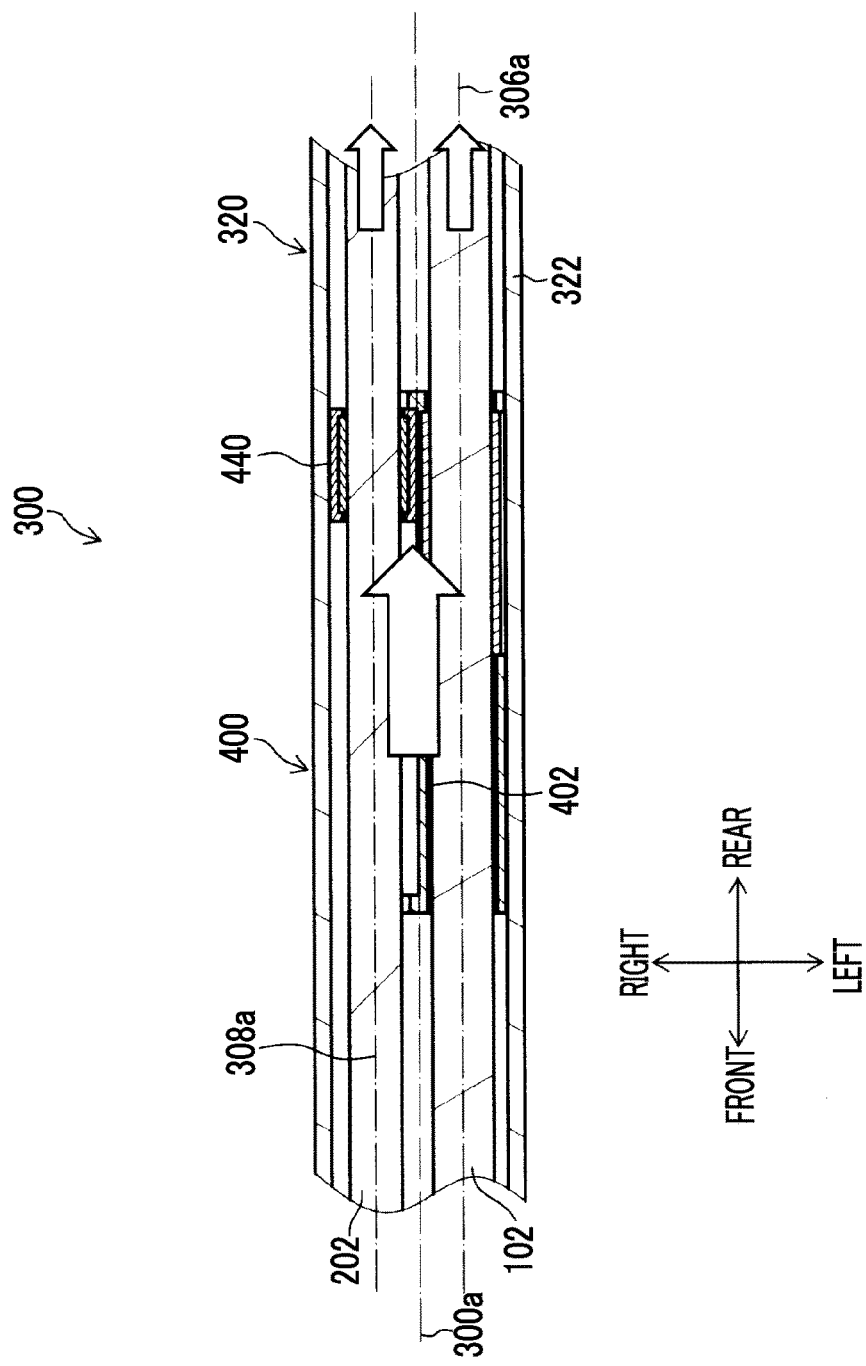
FIG. 12 is an explanatory view used for the description of the action of the slider.

On the other hand, as illustrated in FIG. 12, if the treatment tool insertion part 202 is moved backward in a state where the sleeve 440 reaches the rear end of the movable range thereof with respect to the slider body 402, the sleeve 440 and the slider body 402 move backward with respect to the overtube body 320 together with the treatment tool insertion part 202. Accordingly, the endoscope insertion part 102 moves backward in an interlocking manner with the treatment tool insertion part 202.

Figure 13:
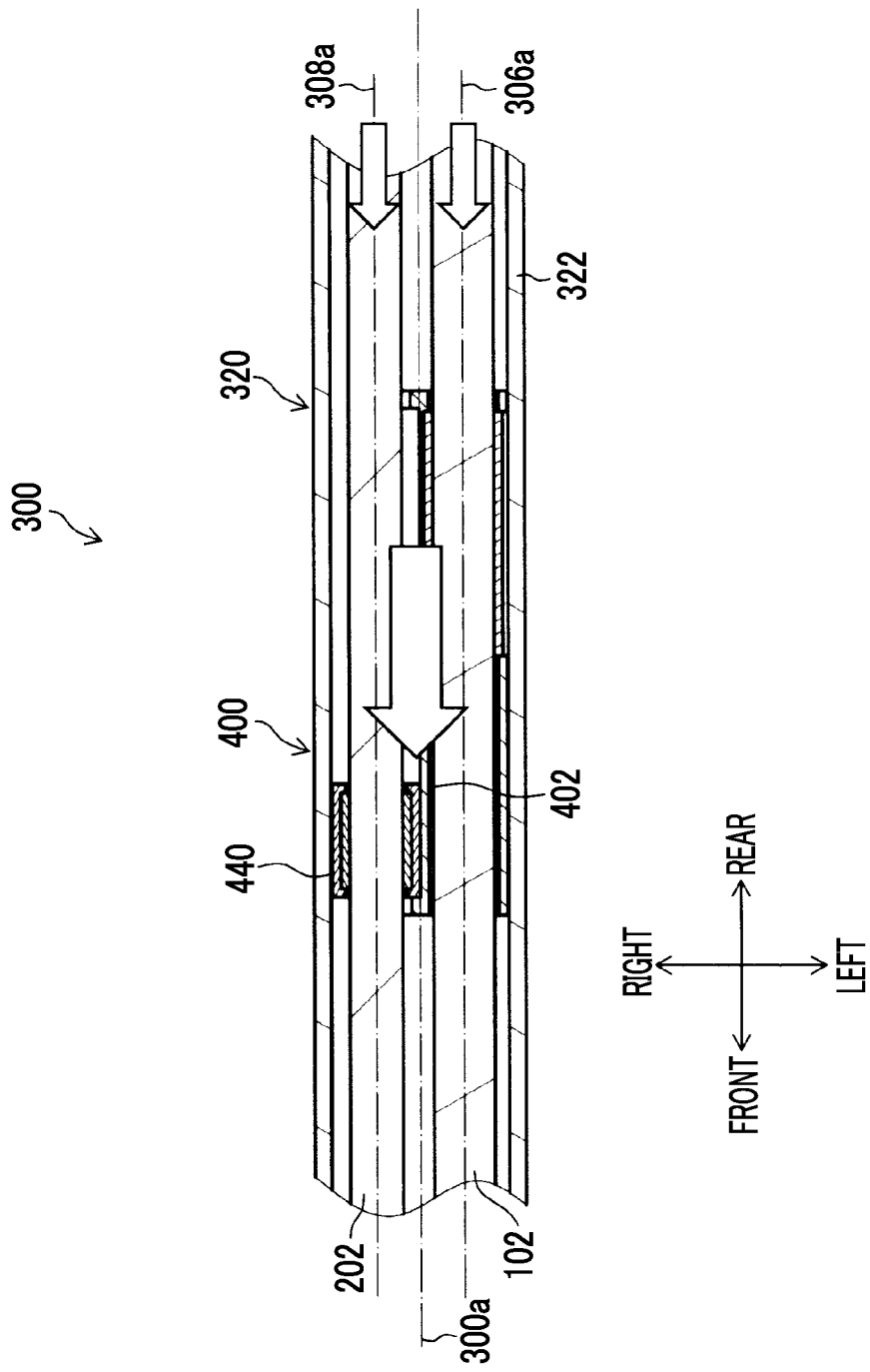
FIG. 13 is an explanatory view used for the description of the action of the slider.

Similarly, as illustrated in FIG. 13, if the treatment tool insertion part 202 is moved forward in a state where the sleeve 440 reaches the front end of the movable range thereof with respect to the slider body 402, the sleeve 440 and the slider body 402 move forward with respect to the overtube body 320 together with the treatment tool insertion part 202. Accordingly, the endoscope insertion part 102 moves forward in an interlocking manner with the treatment tool insertion part 202.

Therefore, when the treatment tool insertion part 202 has been largely displaced in the axial direction as described above (when the forward and backward movement of a large amplitude has been performed), the endoscope insertion part 102 is displaced in the axial direction in an interlocking manner with the treatment tool insertion part 202, and when the displacement of the treatment tool insertion part 202 in the axial direction is small (when the forward and backward movement of a small amplitude is performed), the endoscope insertion part 102 is not displaced in the axial direction.

Figure 14:
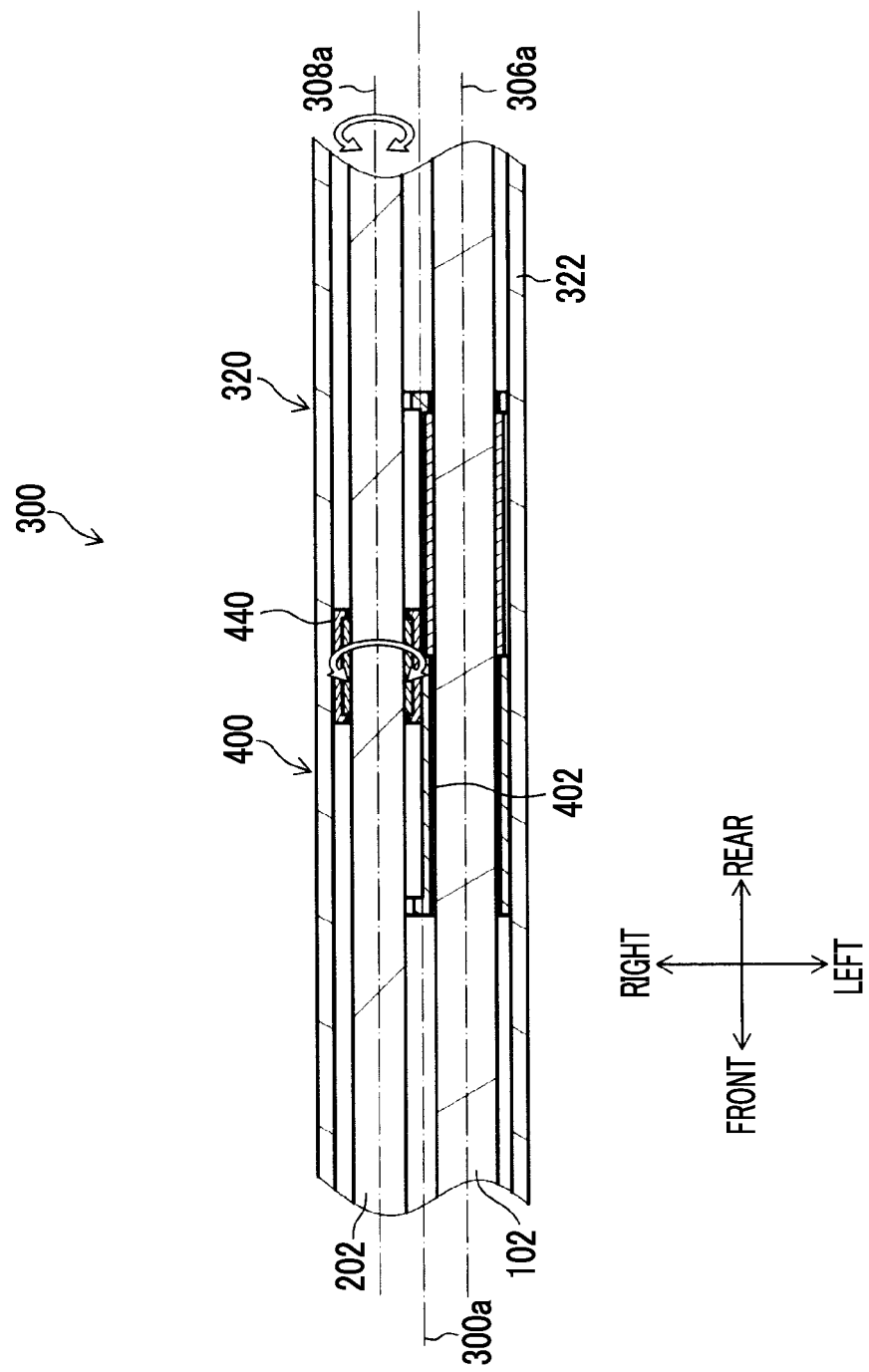
FIG. 14 is an explanatory view used for the description of the action of the slider.

Additionally, in the present embodiment, the slider body 402 is restricted only in forward and backward movement in the forward-rearward direction, whereas the sleeve 440 is supported so as to be rotatable around the axis with respect to the slider body 402. Therefore, as illustrated in FIG. 14, when the treatment tool insertion part 202 is operated to rotate around the axis, the slider body 402 does not rotate, and the treatment tool insertion part 202 and the sleeve 440 rotate around the axis.

Therefore, the rotational angle of the treatment tool insertion part 202 around the axis can be changed, without changing the positions of the endoscope insertion part 102 and the treatment tool insertion part 202 (the positions thereof within a body cavity) with respect to the overtube 300.

That is, when a treatment is performed on a predetermined affected part by inserting the endoscope insertion part 102 and the treatment tool insertion part 202 through the overtube 300 inserted into a body wall, in a general procedure, the endoscope 100 is used such that the position of the endoscope insertion part 102 in the upward-downward direction and in the leftward-rightward direction and the rotational angle thereof around the axis are fixed.

Meanwhile, the rotational operation of the treatment tool insertion part 202 around the axis is appropriately performed similar to the forward and backward movement so that the treatment tool 200 is easily operated by a surgeon.

In the overtube 300 of the present embodiment, the endoscope insertion part 102 and the treatment tool insertion part 202 are coupled by the slider 400. Thus, there is a concern that the positions of the endoscope insertion part 102 in the upward-downward direction and in the leftward-rightward direction and the rotational angle thereof around the axis may fluctuate due to the rotational operation or the like of the treatment tool insertion part 202.

However, since operations other than the forward and backward movement of the slider 400 are restricted as described above, the treatment tool insertion part 202 can be rotated around the axis without changing the positions of the endoscope insertion part 102 in the upward-downward direction and in the leftward-rightward direction and the rotational angle thereof around the axis, and the degree of freedom (five degrees of freedom) required for the operation of forceps is obtained. In addition, the five degrees of freedom of the operation of the forceps are the movement of the forceps with respect to an internal organ, and indicate five movements of the forceps including the movements of the forceps in the longitudinal direction, the transverse direction, and the forward and backward movement direction, the rotation of the forceps, and the opening/closing operation of the forceps.

(Operating Conditions of Slider)

Next, the operating conditions of the slider 400 will be described. Here, forces that act on the respective members related to the operation of the slider 400 are defined as follows.

A force with which the pressure-contact member 426 of the endoscope-coupled part 420 fixes the endoscope insertion part 102 at a fixed position of the outer peripheral surface thereof is referred to as a fixing force for fixing he slider body 402 to the endoscope insertion part 102, and the magnitude of the fixing force (the fixing force for fixing the endoscope insertion part 102 at the fixed position in the axial direction) with respect to the axial direction (forward-rearward direction) is defined as F1.

Similarly, a force with which the pressure-contact member 446 of the sleeve 440 in the treatment tool-coupled part 422 fixes the treatment tool insertion part 202 at a fixed position of the outer peripheral surface thereof is referred to as a fixing force for fixing the sleeve 440 to the treatment tool insertion part 202, and the magnitude of the fixing force with respect to the axial direction (forward-rearward direction) is defined as F2.

Meanwhile, a frictional force received from the valve member 346 when the endoscope insertion part 102 moves forward and backward is defined as F3, and a frictional force received from the valve member 348 when the treatment tool insertion part 202 moves forward and backward is defined as F4.

Additionally, a frictional force received from a peripheral member when the sleeve 440 moves forward and backward with respect to the slider body 402 is defined as F5, and a frictional force received from the peripheral member when the slider body 402 moves forward and backward with respect to the overtube body 320 is defined as F6.

(a) Conditions in which Endoscope and Treatment Tool are Interlocked with Each Other when Forward and Backward Movement Width of Treatment Tool is Large When the treatment tool insertion part 202 has been moved forward and backward (when the treatment tool insertion part has been markedly moved forward and backward), as conditions in which the endoscope insertion part 102 and the treatment tool insertion part 202 are integrally moved forward and backward via the slider 400, the fixing forces F1 and F2, and the frictional force F3 satisfy the following conditions (1) and (2).

$$F1 > F3 \tag{1}$$

$$F2 > F3 \tag{2}$$

Accordingly, if the sleeve 440 reaches the rear end or the front end of the movable range thereof with respect to the slider body 402 as illustrated in FIG. 12 or 13 when the treatment tool insertion part 202 has been moved forward and backward, the sleeve 440 receives the frictional force F3 of the valve member 346 via the slider body 402 and the endoscope insertion part 102. In this case, since the endoscope insertion part 102 and the slider body 402 are coupled by a larger fixing force F1 than the frictional force F3 and the treatment tool insertion part 202 and the sleeve 440 are coupled by a larger fixing force F2 than the frictional force F3, the slider body 402 moves forward and backward in an interlocking manner with the forward and backward movement of the treatment tool insertion part 202, and the endoscope insertion part 102 moves forward and backward in an interlocking manner with the forward and backward movement of the slider body 402.

Therefore, when the treatment tool insertion part 202 has been moved forward and backward, there is no case where, due to the frictional force of the valve member 346, the engagement position of the endoscope insertion part 102 engaged with the slider body 402 shifts and the engagement position of the treatment tool insertion part 202 engaged with the sleeve 440 also shifts.

In addition, when the treatment tool insertion part 202 has been moved forward and backward, as a condition for moving the slider body 402 forward and backward with respect to the overtube body 320 in an interlocking manner with this operation, the fixing force F2 and the frictional force F6 satisfy the following condition (3).

$$F2 > F6 \tag{3}$$

Similarly, when the endoscope insertion part 102 has been moved forward and backward, in order to move the endoscope insertion part 102 and the treatment tool insertion part 202 forward and backward integrally via the slider 400, the fixing forces F1 and F2, and the frictional force F4 satisfy the following conditions (4) and (5).

$$F1 > F4 \tag{4}$$

$$F2 > F4 \tag{5}$$

Additionally, when the endoscope insertion part 102 has been moved forward and backward, as a condition for moving the slider body 402 forward and backward with respect to the overtube body 320 in an interlocking manner with this operation, the fixing force F1 and the frictional force F6 satisfy the following condition (6).

$$F1 > F6 \tag{6}$$

(b) Conditions in which Endoscope and Treatment Tool are not Interlocked with Each Other when Forward and Backward Movement Width of Treatment Tool is Small When the treatment tool insertion part 202 has been moved forward and backward with a small width, as a condition for moving only the treatment tool insertion part 202 forward and backward without moving the endoscope insertion part 102 forward and backward as illustrated in FIG. 11, the frictional forces F3, F5, and F6 satisfy the following condition (7).

$$F3 + F6 > F5 \tag{7}$$

As a result, as illustrated in FIG. 11, when the movement width of the treatment tool insertion part 202 is small, the endoscope insertion part 102 does not move, and when the forward and backward movement width of the treatment tool insertion part 202 is large, the endoscope insertion part 102 moves. That is, when the forward and backward movement width of the treatment tool insertion part 202 is small, the sleeve 440 moves forward and backward only within the slider body 402, and the slider body 402 itself does not move with respect to the overtube body 320. Thus, the endoscope insertion part 102 does not move forward and backward in the axial direction (forward-rearward direction).

In addition, since F6 is considered to be substantially 0 when the frictional resistance of the slider body 402 with respect to the overtube body 320 is small enough to be ignored compared to the frictional force between the endoscope insertion part 102 and the valve member 346, the condition (7) becomes F3>F5.

On the other hand, when the forward and backward movement width of the treatment tool insertion part 202 is large, the sleeve 440 moves forward and backward within the slider body 402, is struck against the distal end side or the base end side of the slider body 402 and moves the slider body 402 itself with respect to the overtube body 320. Thus, the endoscope insertion part 102 coupled to the slider body 402 also moves forward and backward.

(c) Conditions for Adjustment of Length of Treatment Tool Insertion Part 202

As a condition for adjusting the length of the treatment tool insertion part 202 while gripping the endoscope 100 and the treatment tool 200, it is preferable that the fixing forces F1 and F2 satisfy the following condition (8).

$$F1 > F2 \tag{8}$$

Accordingly, even when the treatment tool insertion part 202 has been moved forward and backward using the overtube body 320 or even when the treatment tool insertion part 202 has been moved forward and backward using the endoscope insertion part 102, the engagement position of the treatment tool insertion part 202 using the slider body 402 can be changed without changing the engagement position of the endoscope insertion part 102 engaged with the slider body 402.

When the length of the treatment tool insertion part 202 is adjusted by moving the treatment tool insertion part 202 forward and backward using the overtube body 320, frictional forces are generated between the sleeve 440 and the treatment tool insertion part 202 and between the valve member 348 and the treatment tool insertion part 202. Thus, the operating force required for the forward and backward movement of the treatment tool insertion part 202 is F2+F4. Therefore, in order to allow a surgeon to perform such an adjustment operation without feeling stress, it is desirable that the fixing force F2 and the frictional force F4 satisfy the following condition (9).

$$F2 + F4 < 10 \text{ N (N is Newtons)} \tag{9}$$

Meanwhile, when the length of the treatment tool insertion part 202 is adjusted by moving the treatment tool insertion part 202 forward and backward using the endoscope insertion part 102, if F4<F3 is satisfied, the same frictional forces as above are generated. Thus, it is desirable to satisfy Expression (9). If F3<F4 is satisfied, frictional forces are generated between the sleeve 440 and the treatment tool insertion part 202 and between the valve member 346 and the endoscope insertion part 102. Thus the operating force required for the forward and backward movement of the treatment tool insertion part 202 is F2+F3. Therefore, in order to allow a surgeon to perform such an adjustment operation without feeling stress, it is desirable that the fixing force F2 and the frictional force F3 satisfy the following condition (10).

$$F2+F3<10 \text{ N (N is Newtons)} \quad (10)$$

The invention is effective not only when both of the condition (9) and the condition (10) are satisfied but also when only any one of these conditions is satisfied. In addition, even when the fixing forces F1 and F2 satisfy the following Expression (11), the length of the treatment tool insertion part 202 can be adjusted. In this case, however, the engagement position between the endoscope insertion part 102 and the slider body 402 may move, and the positional adjustment between the slider body 402 and the endoscope insertion part 102 may be separately required.

$$F1<F2 \quad (11)$$

In order to allow a surgeon to perform such an adjustment operation without feeling stress, it is desirable that the fixing force F1 and the frictional force F3 or F4 satisfy the following condition (12) or (13).

$$F1+F4<10 \text{ N (N is Newtons)} \quad (12)$$

$$F1+F3<10 \text{ N (N is Newtons)} \quad (13)$$

(d) Conditions for Securing Excellent Operability

As a condition in which a surgeon can perform the forward and backward movement of the treatment tool insertion part 202 without feeling stress, it is preferable that the frictional forces F3, F4, and F6 satisfy the following condition (14).

$$F3+F4+F6<10 \text{ N (N is Newtons)} \quad (14)$$

In this way, by setting the required operating force (F3+F4+F6) when a surgeon moves the treatment tool insertion part 202 forward and backward markedly, a surgeon can secure excellent operability without feeling stress.

(e) Conditions for Preventing Overtube from Shifting with Respect to Body Wall

As a condition in which the overtube 300 (overtube body 320) is prevented from shifting due to the forward and backward movement of the treatment tool insertion part 202, if the fixing force of the overtube 300 in the forward-rearward direction (axial direction) with respect to a body wall is defined as Ft, the fixing force Ft and the frictional forces F3 and F4 satisfy the following condition (15).

$$Ft>F3+F4 \quad (15)$$

Accordingly, even if the treatment tool insertion part 202 has been moved forward and backward, the overtube 300 (overtube body 320) inserted into a body wall is fixed in a stable state without shifting. Thus, it is possible to secure excellent operability.

(Other Forms of Slider)

In the above overtube 300, a supporting mechanism of the slider 400 adapted to be capable of moving the slider 400 forward and backward only in the forward-rearward direction with respect to the overtube body 320 is not limited to the above form.

Figure 15:
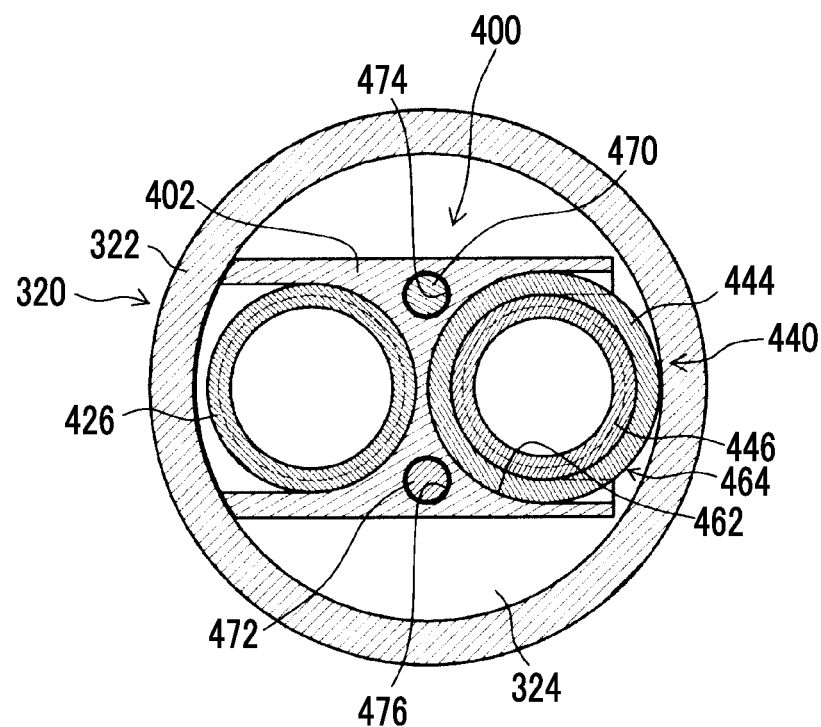
FIG. 15 is a sectional view illustrating another embodiment of the supporting mechanism of the slider in the overtube.

FIG. 15 is a sectional view illustrating another form of the overtube 300 by the section orthogonal to the reference axis 300a. In addition, the same reference signs will be given to constituent elements of the same or similar actions as those of the above form, and the description thereof will be omitted.

In the form illustrated in this drawing, guide rods 470 and 472, which are laid from the base end (base end cap 340) to the distal end (distal end cap 360), are arranged along the direction of the reference axis 300a at the upper part and the lower part within the lumen 324 of the overtube body 320.

Meanwhile, guide holes 474 and 476, which penetrate from the base end to the front end, are formed at the upper part and the lower part of the slider body 402 of the slider 400.

The guide rods 470 and 472 are respectively inserted through the guide holes 474 and 476, and the slider 400 is supported within the lumen 324.

Accordingly, the slider 400 is supported so as to be movable forward and backward only in the forward-rearward direction with respect to the overtube body 320.

Figure 16:
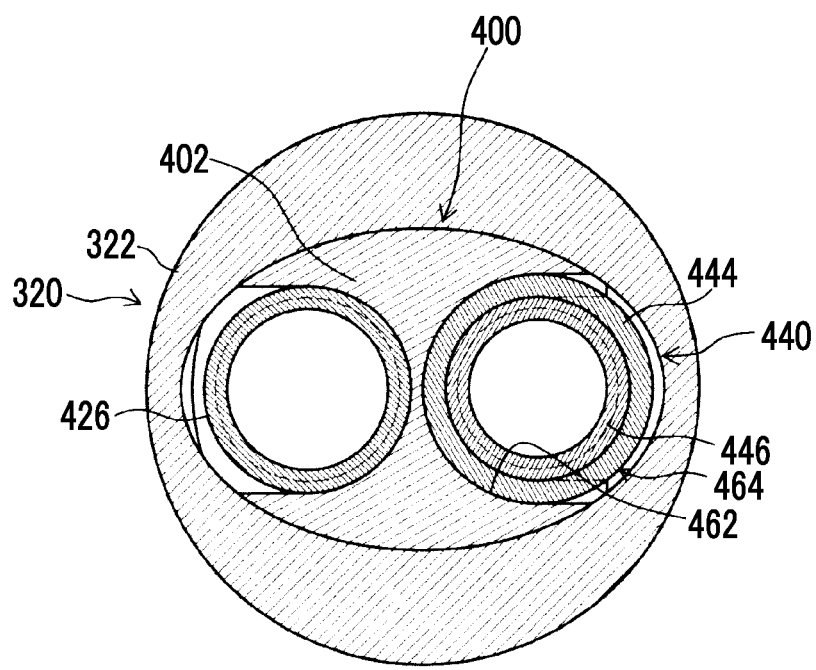
FIG. 16 is a sectional view illustrating another embodiment of the supporting mechanism of the slider in the overtube.

FIG. 16 is a sectional view illustrating still another form of the overtube 300 by the section orthogonal to the reference axis 300a. In addition, the same reference signs will be given to constituent elements of the same or similar actions as those of the above form, and the description thereof will be omitted.

As illustrated in this drawing, the inner peripheral surface of the overtube body 320 (outer wall 322), that is, the outer shape of the lumen 324, is formed in an elliptical shape in the section orthogonal to the reference axis 300a.

Meanwhile, the slider 400 is formed so that the outer peripheral surface of the slider body 402 that is a frame body has a shape along an ellipse of the same shape as the lumen 324 in the section orthogonal to the reference axis 300a and the outer peripheral surface of the slider body 402 comes in contact with or approaches the inner peripheral surface of the overtube body 320.

Accordingly, the slider 400 is supported so as to be movable forward and backward only in the forward-rearward direction with respect to the overtube body 320.

In addition, the shape of the slider is not limited to this, and the shape of the inner peripheral surface of the overtube body 320 and the shape of the slider body 402 in the section orthogonal to the reference axis 300a only has to be a combination of non-rotatable shapes. For example, in the forms illustrated in FIGS. 7 and 15, if the shape of the inner peripheral surface of the overtube body 320 is formed in an elliptical shape as illustrated in FIG. 16 and the inner peripheral surface of the overtube body 320 is circumscribed on the slider body 402, similar to the form of FIG. 16, special guide means, such as the form of the protruding strips 408 and 410, the guide plates 374 and 376 in the form of FIG. 7 and the guide rods 470 and 472 and the guide holes 474 and 476 in the form of FIG. 15, can be made unnecessary.

(Description of Inner Needle)

Next, an inner needle 500 to be used after being mounted on the overtube 300 when the overtube 300 is inserted into a body wall will be described.

Figure 17:
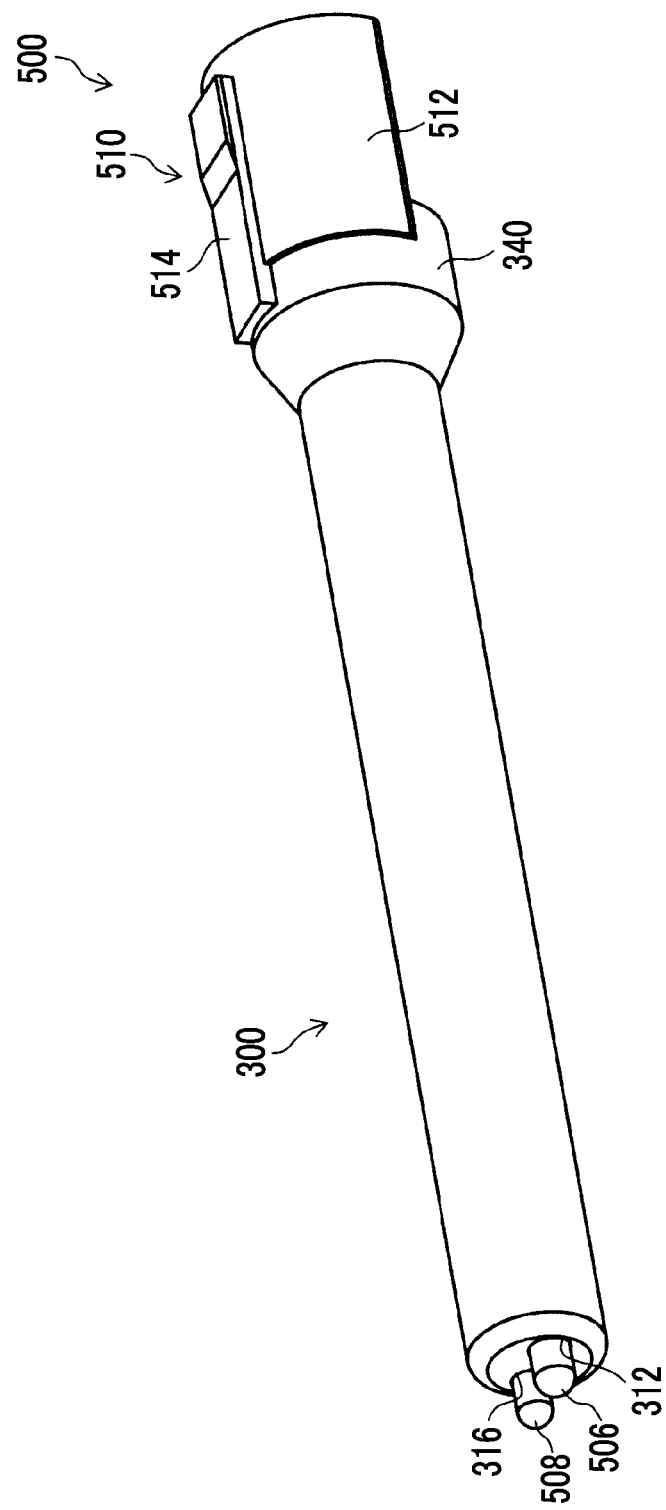
FIG. 17 is a perspective view illustrating a state where an inner needle has been mounted on the overtube, from the front upper left.
Figure 18:
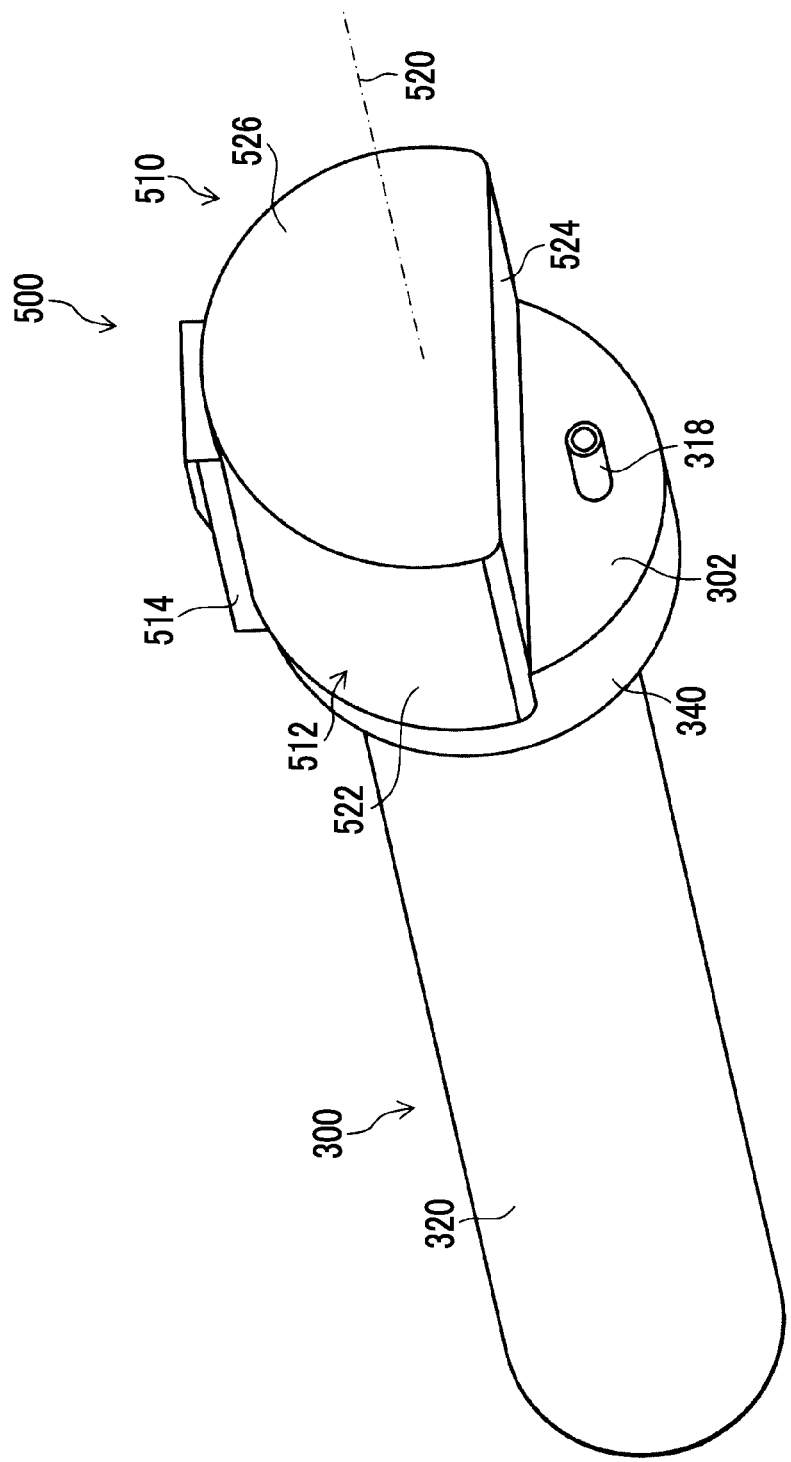
FIG. 18 is a perspective view illustrating a state where the inner needle has been mounted on the overtube, from the rear lower left.
Figure 19:
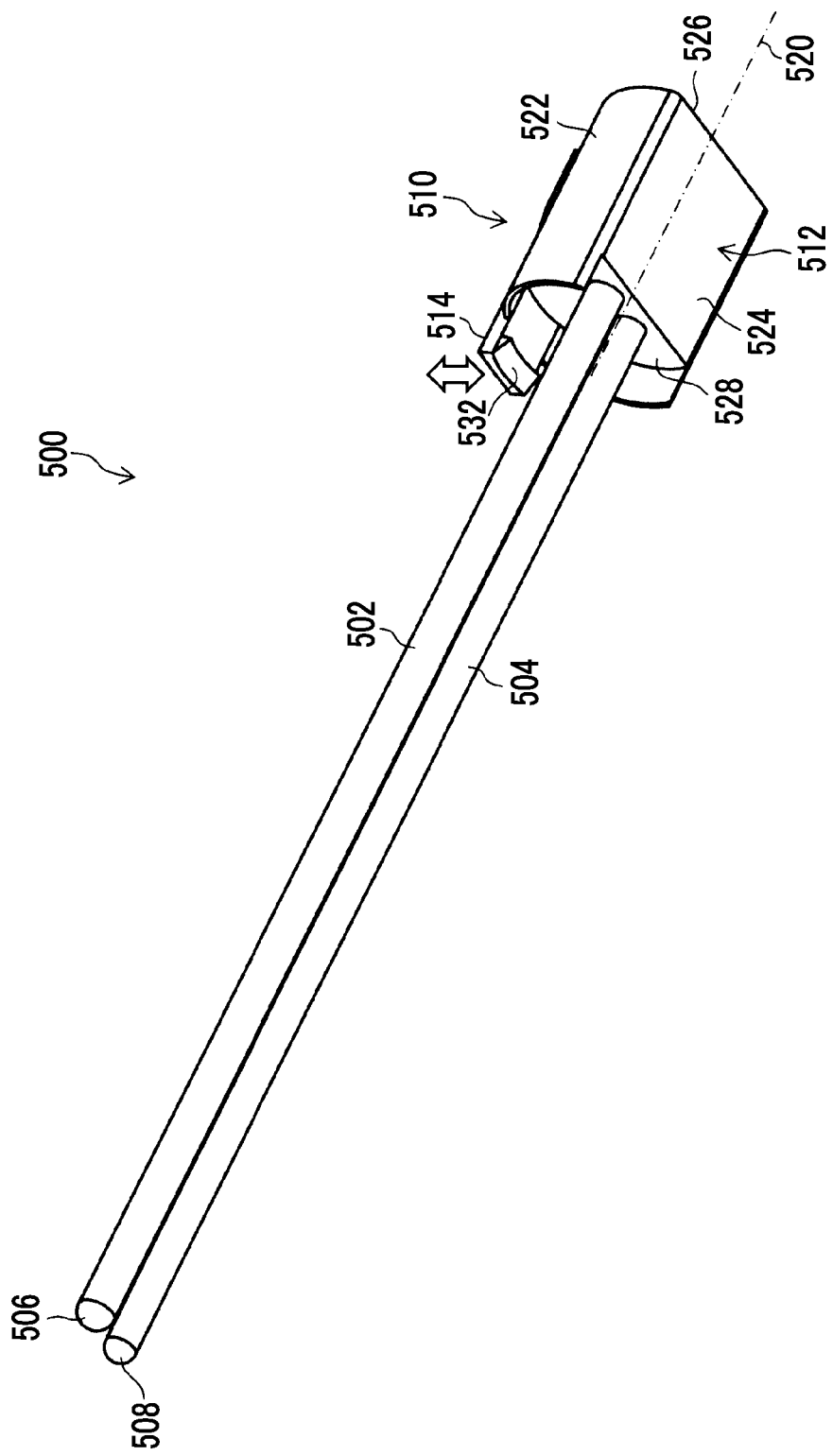
FIG. 19 is a perspective view illustrating the inner needle from the front lower left.

FIGS. 17 and 18 are respectively perspective views illustrating a state where the inner needle 500 has been mounted on the overtube 300 from the front upper left and from the rear lower left, and FIG. 19 is a perspective view illustrating only the inner needle 500 from the front lower left. In addition, the relationship of front and rear, left and right, and up and down of the inner needle 500 follows the relationship of front and rear, left and right, up and down of the overtube 300 when being mounted on the overtube 300 as illustrated in FIG. 17.

As illustrated in these drawings, the inner needle 500 is constituted of two shaft parts 502 and 504 that are formed in an elongated shape, distal end parts 506 and 508 that are respectively formed at the distal ends of the shaft parts 502 and 504, and a head part 510 that is provided on the base end sides of the shaft parts 502 and 504.

The shaft part 502 (first shaft part) has a diameter equal to or smaller than the external diameter of the above-described endoscope insertion part 102, and is formed with a size such that the shaft part is insertable through the endoscope insertion passage 306. As illustrated in FIGS. 17 and 18, when the inner needle 500 is mounted on (incorporated into) the overtube 300, the shaft part 502 is arranged so as to be inserted through the endoscope insertion passage 306 of the overtube 300.

Additionally, the shaft part 502 is formed to be slightly longer than the length of the overtube 300 (endoscope insertion passage 306) in the forward-rearward direction, and when the inner needle 500 has been mounted on the overtube 300, the distal end part 506 of the shaft part 502 protrudes by a predetermined length from the endoscope delivery opening 312.

The shaft part 504 (second shaft part) has a diameter equal to or smaller than the external diameter of the above-described treatment tool insertion part 202, and is formed with a size such that the shaft part is insertable through the treatment tool insertion passage 308. As illustrated in FIGS. 17 and 18, when the inner needle 500 has been mounted on the overtube 300, the shaft part 504 is arranged so as to be inserted through the treatment tool insertion passage 308 of the overtube 300.

Additionally, the shaft part 504 is formed to be slightly longer than the length of the overtube 300 (treatment tool insertion passage 308) in the forward-rearward direction, and when the inner needle 500 has been mounted on the overtube 300, the distal end part 508 of the shaft part 504 protrudes by a predetermined length from the treatment tool delivery opening 316.

Although the distal end parts 506 and 508 are formed in a curved surface shape and are configured to be dull so that no edge is formed (that is, in a rounded non-edge shape), the distal end parts are adapted to be capable of penetrating a body wall easily.

The head part 510 has a head part body 512 and a locking lever 514.

The head part body 512, as illustrated in FIGS. 18 and 19, has a shape surrounded by a side surface 522 along a column surface having an axis 520 extending in the forward-rearward direction in parallel with the shaft parts 502 and 504 as a center having a diameter that approximately coincides with the external diameter of the base end cap 340 of the overtube 300, a lower surface 524 along a plane which is parallel to the axis 520 (parallel to the forward-rearward direction and the leftward-rightward direction) and which intersects the column surface along which the side surface 522 runs, and the rear end surface 526 and a front end surface 528 along a plane orthogonal to the axis 520.

In addition, the axis 520 is arranged coaxially with the reference axis 300a (not illustrated) of the overtube 300 in a state where the inner needle 500 has been mounted on the overtube 300.

The front end surface 528 of the head part body 512 has the base end sides of the shaft parts 502 and 504 fixed thereto, and the side surface 522 of the head part body 512 has the locking lever 514 provided along the direction (forward-rearward direction) of the axis 520 at a central part (topmost part) thereof in the circumferential direction.

The locking lever 514 is a constituent element of a fixing mechanism that detachably fixes the head part 510 of the inner needle 500 to the overtube 300, is formed in an elongated plate shape extending along the direction of the axis 520 (refer to FIG. 17), and is supported by the head part body 512 so as to be turnable in such an orientation that a front end part and a rear end part are opposite to each other in the upward-downward direction with the vicinity of the center in the direction of the axis 520 as a fulcrum.

A locking claw 532 (refer to FIG. 19) is provided to protrude from a lower surface side of a distal end part of the locking lever 514, and the locking claw 532, as illustrated in FIGS. 3 and 5, has such a shape that the locking claw is fitted to a locking hole 534 provided in the base end cap 340.

Additionally, a biasing member, such as a coil spring, is arranged at the head part body 512 at a position on a lower surface side of a base end part of the locking lever 514, and the locking lever 514 is biased so that the rear end part faces up and the front end part faces down.

(Action when Inner Needle is Mounted)

Figure 20:
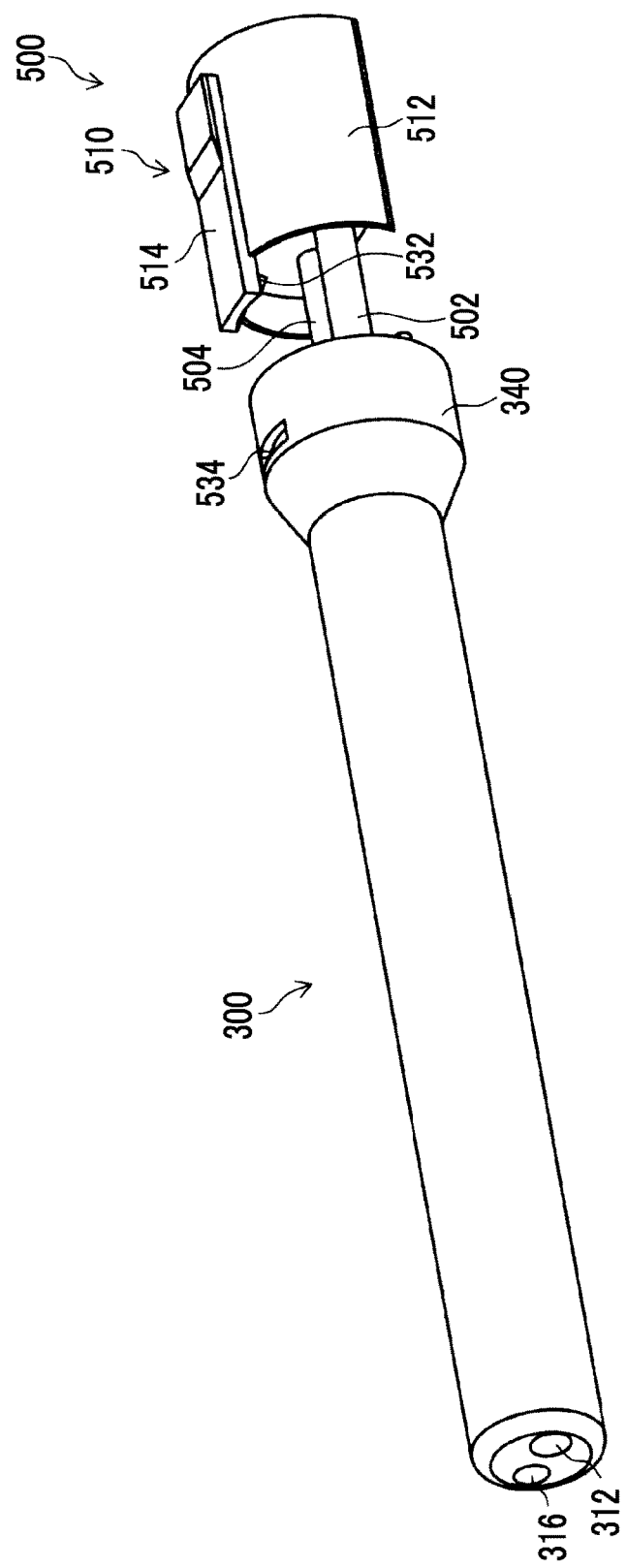
FIG. 20 is a perspective view illustrating a situation in which the inner needle is mounted on the overtube.

According to the inner needle 500 configured as above, if the shaft parts 502 and 504 of the inner needle 500 are respectively inserted into the endoscope insertion passage 306 and the treatment tool insertion passage 308 from the endoscope insertion opening 310 and the treatment tool insertion opening 314, respectively, of the overtube 300, as illustrated in FIG. 20, the head part 510 of the inner needle 500 approaches the base end cap 340 of the overtube 300.

Then, if the inner needle 500 is further inserted, as illustrated in FIGS. 17 and 18, the front end surface 528 of the head part body 512 abuts against the base end surface 302 of the overtube 300 (base end cap 340), and the locking claw 532 of the locking lever 514 is fitted to the locking hole 534 of the base end cap 340 and is brought into a state where the inner needle 500 has been mounted on (fixed to) the overtube 300.

In this case, the distal end parts 506 and 508 of the shaft parts 502 and 504 of the inner needle 500 are arranged so as to protrude by a predetermined length from the distal end of the overtube 300.

Meanwhile, if the base end part of the locking lever 514 is pressed in a state where the inner needle 500 has been mounted on the overtube 300, the locking claw 532 can be removed from the locking hole 534 of the base end cap 340, and if the inner needle 500 is pulled out to the hand side in that state, the inner needle 500 can be detached from the overtube 300.

Additionally, as described above, the head part body 512 of the inner needle 500 has such a shape that a lower side of a columnar member is cut out by the lower surface 524. That is, the head part body 512 is provided with a cutout part formed by cutting out a portion that interferes with the air supply connector 318 when the inner needle 500 has been mounted on the overtube 300.

Accordingly, the front end surface 528 of the head part body 512 can be made to abut against the base end surface 302 without interfering with the air supply connector 318 provided to protrude from the base end surface 302 of the overtube 300 (base end cap 340) as illustrated in FIG. 18 when the inner needle 500 has been mounted on the overtube 300, and the inner needle 500 can be mounted on the overtube 300 in a stable state.

In addition, the invention is not limited to the above form, and the head part body 512 only has to have the cutout part formed by cutting out the portion of the head part body 512 that interferes with at least the air supply connector 318 when the inner needle 500 has been mounted on the overtube 300. Additionally, since the rotation of the head part body 512 is restricted with respect to the overtube 300 by the shaft parts 502 and 504, the head part body does not interfere with the air supply connector 318.

(Conditions for Preventing Endoscope Insertion Part from Entering Overtube)

Next, the characteristic parts of the invention will be described. In addition, in the following, the same reference signs will be used for constituent elements of the same or similar actions as the constituent elements in the above basic configuration, and the description thereof will be omitted, and only differences from the above basic configuration will be described.

In the overtube 300 and the endoscope 100 in the basic configuration of the above-described endoscopic surgical device 10, the surgeon or the like can freely change the engagement position of the endoscope insertion section 102 engaged with the slider 400 (slider body 402).

In addition, in the following, the engagement position of the endoscope insertion part 102 is mainly referred to as a coupling position, and represents the position of the endoscope insertion part 102 to which the endoscope-coupled part 420, illustrated in FIG. 10 and the like, of the slider 400 is coupled.

Meanwhile, the coupling position of the endoscope insertion section 102 with respect to the slider 400 can be freely changed. Thus, for example, when the treatment tool insertion part 202 has been moved backward in a state where the endoscope insertion part 102 and the treatment tool insertion part 202 are respectively inserted through the endoscope insertion passage 306 and the treatment tool insertion passage 308 of the overtube 300, there is a possibility that the distal end (distal end surface 114) of the endoscope insertion part 102 that has moved backward in an interlocking manner with the backward movement of the treatment tool insertion part 202 may enter the inside (a portion closer to the base end side than the endoscope delivery opening 312) of the overtube 300.

If the distal end of the endoscope insertion part 102 enters the inside of the overtube 300, the observation visual field of the endoscope 100 is blocked by the overtube 300, and a malfunction such that treatment cannot be performed occurs.

Additionally, when the distal end of the endoscope insertion part 102 has been soiled, the work of inserting the endoscope insertion part 102 into the overtube 300 is performed after the endoscope insertion part 102 has first been extracted from the overtube 300 and cleaned.

In this case, in order to return the positional relationship in the axial direction between the distal end (treatment part 206) of the treatment tool insertion part 202 and the distal end of the endoscope insertion part 102 to an original state, it is necessary to set the coupling position of the endoscope insertion part 102 with respect to the slider 400 to an original position.

However, since the slider 400 is movable forward and backward with respect to the overtube body 320, there is a problem in that the coupling position of the endoscope insertion part 102 with respect to the slider 400 cannot be precisely grasped and it is difficult to return the coupling position to the original position.

Thus, the endoscopic surgical device 10 in the present embodiment has a configuration in which these problems can be solved.

FIG. 21 is a sectional view illustrating the overtube 300 in the endoscopic surgical device 10 to which that the invention is applied, and illustrating a state where the slider body 402 has been arranged at the rear end of the movable range thereof with respect to the overtube body 320 in a state where the endoscope insertion part 102 and the treatment tool insertion part 202 have been inserted through the endoscope insertion passage 306 and the treatment tool insertion passage 308 of the overtube 300.

First, the coupling position of the endoscope-coupled part 420 with respect to the slider 400 in the direction of the reference axis 300*a* is defined as the position (a position that faces a rear end 426*e*) of the rear end 426*e* of the pressure-contact member 426 of the slider 400.

As illustrated in this drawing, the length from the coupling position of the endoscope insertion part 102 to the distal end (distal end surface 304) of the overtube 300 in a state where the slider body 402 is arranged at the rear end of the movable range thereof with respect to the overtube body 320 is defined as L.

In contrast, the coupling position of the endoscope insertion part 102 is set to a position where the length Ls from the coupling position to the distal end (distal end surface 114) of the endoscope insertion part 102 satisfies the following condition (16).

$$Ls \geq L \tag{16}$$

Accordingly, even when the slider body 402 has moved to the rear end of the movable range as illustrated in FIG. 21, the slider body 402 is arranged at a position where the distal end of the endoscope insertion part 102 coincides with the distal end of the overtube 300 or a position where the distal end of the endoscope insertion part 102 protrudes further forward than the distal end of the overtube 300.

Therefore, a situation where the distal end of the endoscope insertion part 102 enters the inside of the overtube 300 is prevented beforehand.

In addition, although the coupling position of the endoscope insertion part 102 with respect to the slider 400 has been set to the position of the rear end 426*e* of the pressure-contact member 426, the above condition (16) is satisfied even in a case where positions other than the rear end 426*e* of the pressure-contact member 426 are defined as the coupling position. However, the length L hereinbelow indicates the length from the position of the rear end 426*e* of the pressure-contact member 426 to the distal end of the overtube 300.

Additionally, by configuring the invention so that the coupling position of the endoscope insertion part 102 can be set to a specific position that satisfies the condition (16), even in a case where the endoscope insertion part 102 is inserted into the overtube 300 after the endoscope insertion part 102 has first been extracted from the overtube 300, the coupling position of the endoscope insertion part 102 can easily be reset to the original position.

(Configuration Example for Preventing Endoscope Insertion Part from Entering Overtube)

FIG. 22 is a plan view illustrating the endoscope 100 in the endoscopic surgical device 10 to which the invention is applied.

As illustrated in this drawing, the endoscope insertion part 102 of the endoscope 100 has a stepped part 154 at a predetermined position, a smaller-diameter part 150 located closer to the distal end side than the stepped part 154, and a larger-diameter part 152 located closer to the base end side than the stepped part 154.

The smaller-diameter part 150 has a diameter of a size such that the smaller-diameter part is insertable through the endoscope insertion passage 306 of the overtube 300 but the slider 400 (endoscope-coupled part 420) is not coupled thereto. That is, the smaller-diameter part 150 is smaller than the internal diameter of the pressure-contact member 426 (refer to FIG. 6 and the like) that is an endoscope engagement part of the slider 400, and is not engageable with the pressure-contact member 426.

Additionally, the smaller-diameter part 150 has a length L0 equal to or greater than the above length L (L0≥L).

The larger-diameter part 152 is larger than the smaller-diameter part 150, and has a diameter of a size such that the larger-diameter part is insertable through the endoscope insertion passage 306 of the overtube 300 and is brought into pressure contact with the pressure-contact member 426 of the slider 400 and the slider 400 (endoscope-coupled part 420) is coupled thereto. That is, the larger-diameter part 152 is slightly larger than the internal diameter of the pressure-contact member 426, and is engageable with the pressure-contact member 426, which is a frictional engagement part, through frictional engagement.

The stepped part 154 is formed at a boundary position between the smaller-diameter part 150 and the larger-diameter part 152, and has a coupling surface that is an annular surface orthogonal to the axial direction and couples an outer peripheral surface of the smaller-diameter part 150 and an outer peripheral surface of the larger-diameter part 152.

FIG. 23 is a sectional view illustrating a portion of the overtube 300 immediately after the slider 400 has been coupled to the endoscope insertion part 102 of FIG. 22 in an enlarged manner.

When the endoscope insertion part 102 is inserted into and moved forward to the endoscope insertion passage 306 of the overtube 300 and the endoscope insertion part 102 is coupled to the slider 400, as illustrated in this drawing, the smaller-diameter part 150 of the endoscope insertion part 102 passes through the through-hole 432 of the pressure-contact member 426, without being brought into pressure contact with the pressure-contact member 426 of the slider 400.

Then, if the stepped part 154 reaches the position of the rear end 426e of the pressure-contact member 426, the slider 400 is pushed by the stepped part 154, moves forward together with the endoscope insertion part 102, and moves to the front end of the movable range thereof with respect to the overtube body 320.

In addition, the treatment tool insertion part 202 is released without being gripped.

Thereafter, if the endoscope insertion part 102 is further moved forward, as illustrated in this drawing, the larger-diameter part 152 enters the through-hole 432 of the pressure-contact member 426.

Accordingly, the larger-diameter part 152 is brought into pressure contact with the pressure-contact member 426 and is engaged with the pressure-contact member 426, and the slider 400 is coupled to the endoscope insertion part 102.

In this case, an operator who is performing a forward movement of the endoscope insertion part 102 can detect that the slider 400 has been coupled to the endoscope insertion part 102 because the operating force of the forward movement becomes large. Then, by further moving the endoscope insertion part 102 forward after it is detected that the slider 400 has been coupled to the endoscope insertion part 102, the coupling position of the endoscope insertion part 102 with respect to the slider 400 can be adjusted.

In this way, when the endoscope insertion part 102 of FIG. 22 is inserted into the endoscope insertion passage 306 of the overtube 300 and the endoscope insertion part 102 is coupled to the slider 400, a state where the stepped part 154 of the endoscope insertion part 102 has been arranged closer to the front side than the rear end 426e of the pressure-contact member 426 of the slider 400 is achieved.

Therefore, the length from the position of the rear end 426e of the pressure-contact member 426 to the distal end of the endoscope insertion part 102, that is, the length Ls from the coupling position of the endoscope insertion part 102 illustrated in FIG. 21 to the distal end of the endoscope insertion part 102 becomes equal to or larger than the length L0 of the smaller-diameter part 150 of the endoscope insertion part 102 (Ls≥L0).

As described above, since the length L0 of the smaller-diameter part 150 becomes equal to or larger than the above length L (L0≥L), a state where the above condition (16) is satisfied is set, in a state where the slider 400 has been coupled to the endoscope insertion part 102.

Additionally, if the forward movement of the endoscope insertion part 102 is stopped when the operating force of the forward movement of the endoscope insertion part 102 becomes large as described above, and when it is detected that the slider 400 has been coupled to the endoscope insertion part 102, as illustrated in FIG. 23, the coupling position (the position of the rear end 426e of the pressure-contact member 426) of the endoscope insertion part 102 with respect to the slider 400 substantially coincides with the position of the stepped part 154.

That is, the operator can always set the coupling position of the endoscope insertion part 102 with respect to the slider 400 to the vicinity position of the stepped part 154 according to the operational feeling of the forward and backward movement of the endoscope insertion part 102.

Therefore, if the endoscope insertion part 102 is used after being coupled to the slider 400 at the vicinity position of the stepped part 154, even in a case where the endoscope insertion part 102 has first been extracted from the overtube 300, the coupling position of the endoscope insertion part 102 with respect to the slider 400 can easily be reset to the original position when the endoscope insertion part 102 is inserted into the overtube 300.

As described above, in the endoscope 100 of the above form, the endoscope insertion part 102 is adapted to be capable of being coupled to the slider 400 only at the position of the larger-diameter part 152 located closer to the base end side than the stepped part 154 of the endoscope insertion part 102. However, the invention is not limited to this.

(Another Configuration Example for Preventing Endoscope Insertion Part from Entering Overtube)

FIG. 24 is a plan view illustrating another embodiment of the endoscope 100.

The endoscope insertion part 102 of the endoscope 100 illustrated in this drawing has a diameter of a size that is constant in its entirety, and has a diameter of a size such that the endoscope insertion part is insertable through the endoscope insertion passage 306 of the overtube 300 and is brought into pressure contact with the pressure-contact member 426 of the slider 400 and the slider 400 is coupled thereto. That is, the endoscope insertion part is slightly larger than the internal diameter of the pressure-contact member 426.

Meanwhile, a high-friction part 170 (high friction member) having a higher frictional coefficient than the other portions is provided in an axial partial range of the endoscope insertion part 102.

The high-friction part 170 is provided at a position where the length L1 from the position of a front end thereof to the distal end of the endoscope insertion part 102 becomes equal to or larger than the above length L (L1≥L).

According to this endoscope 100, if the front end of the high-friction part 170 reaches the position of the rear end 426e of the pressure-contact member 426 when the endoscope insertion part 102 is inserted into and moved forward to the endoscope insertion passage 306 of the overtube 300 and is coupled to the slider 400, the high-friction part 170 then enters the through-hole 432 of the pressure-contact member 426. Accordingly, the operator who is performing the forward movement of the endoscope insertion part 102 can detect that the coupling position of the endoscope insertion part 102 with respect to the slider 400 has reached the high-friction part 170 because the operating force of the forward movement becomes large.

In this case, the length from the position of the rear end 426e of the pressure-contact member 426 to the distal end of the endoscope insertion part 102, that is, the length Ls from the coupling position of the endoscope insertion part 102 illustrated in FIG. 21 to the distal end thereof becomes equal to or larger than the above length L1 (Ls≥L1). As a result, a state where the above condition (16) is satisfied is set because the length L1 is equal to or larger than the above length L (L1≥L).

Therefore, if the slider 400 is coupled at a position where the endoscope insertion part 102 has been further moved forward with respect to the slider 400 after it is detected that the coupling position of the endoscope insertion part 102 has reached the high-friction part 170, a state where the above condition (16) is satisfied can be set.

Meanwhile, if the slider 400 is coupled at the position where it is detected that the coupling position of the endoscope insertion part 102 has reached the high-friction part 170, even in a case where the endoscope insertion part 102 has first been extracted from the endoscope insertion passage 306 of the overtube 300, the coupling position of the endoscope insertion part 102 can be easily reset to the original position.

In the above embodiment, the distal end of the endoscope insertion part 102 is adapted so as not to be arranged closer to the base end side than the distal end of the overtube 300 in a state where the slider 400 has been arranged at the rear end of the movable range thereof with respect to the overtube body 320. However, the invention is not limited to this, and the distal end of the endoscope insertion part 102 can be adapted so as not to be arranged closer to the base end side than a reference position, using an arbitrary position other than the distal end of the overtube 300 as the reference position.

(Application to Treatment Tool Insertion Part)

Additionally, the treatment tool insertion part 202 can also be applied similar to the above embodiment regarding the endoscope insertion part 102. That is, the same component parts as the stepped part 154 and the high-friction part 170 of the endoscope insertion part 102 illustrated in FIG. 22 or FIG. 24 may be provided in the treatment tool insertion part 202 so that the distal end of the treatment tool insertion part 202 engaged with the sleeve 440 is not located closer to the base end side than at least the distal end surface 304 of the overtube 300 or a desired reference position, in a state where the slider 400 is arranged at the rear end of the movable range thereof with respect to the overtube body 320 and the sleeve 440 is arranged at the rear end of the movable range thereof with respect to the slider body 402.

<Operation Method of Endoscopic Surgical Device>

Next, an example of operation methods using the endoscopic surgical device 10 of the present embodiment will be described.

FIGS. 25A to 31B are explanatory views illustrating a situation in which the endoscopic surgical device 10 of the present embodiment is operated.

Figure 25A:
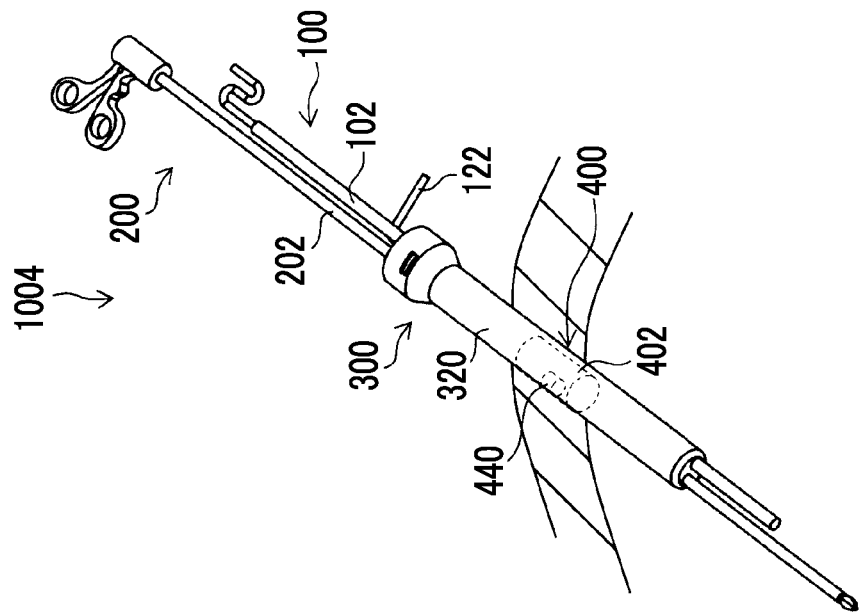
FIGS. 25A to 25C are views illustrating a situation in which the overtube is inserted into a body wall.
Figure 25B:
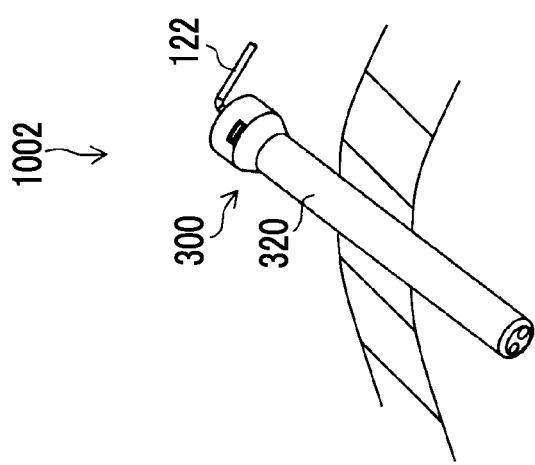
Figure 25C:
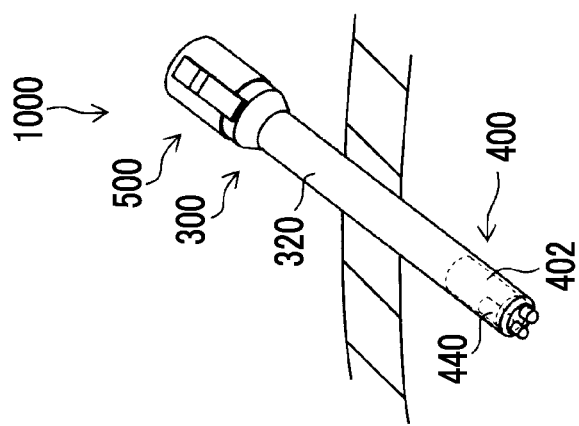

FIGS. 25A to 25C are views illustrating a situation in which the overtube 300 is inserted into a body wall.

FIGS. 26A to 27B are views illustrating a situation in which the treatment tool insertion part 202 is pushed into an affected part side within a body cavity from the hand side.

FIGS. 28A to 29B are views illustrating a situation in which the treatment tool insertion part 202 is pulled to the hand side from the affected part side within the body cavity.

FIGS. 30A to 31B are views illustrating a situation in which the endoscope insertion part 102 is extracted from and re-inserted into the overtube 300.

First, as a preparation process for starting the operation of the endoscopic surgical device 10, the overtube 300 is inserted into a skin incision part (incised wound) formed in a body wall in a state where the inner needle 500 has been mounted on the overtube 300, and the overtube 300 is inserted into the body cavity like a state designated by reference sign 1000 of FIG. 25A.

Next, the inner needle 500 is extracted from the endoscope insertion passage 306 and the treatment tool insertion passage 308 (the inner needle 500 is removed from the overtube 300), and one end part of the air supply tube 122 is connected to the air supply connector 318 of the overtube 300 like a state designated by reference sign 1002 of FIG. 25B. The other end part is connected to the pneumoperitoneum device 120. Then, pneumoperitoneum gas is delivered from the pneumoperitoneum device 120, and the pneumoperitoneum gas is injected into the body cavity through the air supply tube 122 and the overtube 300.

Next, the endoscope insertion part 102 is inserted into the endoscope insertion passage 306 from the endoscope insertion opening 310 of the overtube 300, and the distal end of the endoscope insertion part 102 is led out from the endoscope delivery opening 312.

In this case, for example, when the endoscope 100 illustrated in FIG. 22 is used, the endoscope insertion part 102 is moved forward at least to a position where the slider 400 is coupled to the larger-diameter part 152 of the endoscope insertion part 102, on the basis of an operational feeling for the forward movement as described above. Accordingly, the endoscope insertion part 102 and the slider 400 are brought into a state where they move integrally. Additionally, even in a case where the slider 400 has moved to the rear end of the movable range thereof with respect to the overtube body 320, a situation where the distal end of the endoscope insertion part 102 enters the inside of the overtube 300 is prevented.

Moreover, when the coupling position of the endoscope insertion part 102 with respect to the slider 400 is set so as to be the vicinity of the stepped part 154, it becomes easy to perform setting to the same coupling position again even in a case where the endoscope insertion part 102 is extracted from the overtube 300 for cleaning or the like.

Subsequently, the treatment tool insertion part 202 is inserted into the treatment tool insertion passage 308 from the treatment tool insertion opening 314 of the overtube 300, and the distal end (treatment part 206) of the treatment tool insertion part 202 is led out from the treatment tool delivery opening 316.

In this case, the treatment tool insertion part 202 has the sleeve 440 of the treatment tool-coupled part 422 of the slider 400 inserted therethrough, and is coupled to the sleeve 440 as described above. Accordingly, the treatment tool insertion part 202 and the sleeve 440 are brought into a state where they move integrally.

If the preparation step is performed in this way, a state where the operation of the endoscopic surgical device 10 is operable is brought about like a state designated by reference sign 1004 of FIG. 25C.

In addition, the distal end position of the endoscope insertion part 102 is arranged behind at least the distal end position of the treatment tool insertion part 202 so that the situation of the treatment part 206 at the distal end of the treatment tool insertion part 202 can be observed by the endoscope 100. Additionally, the procedure of inserting the endoscope insertion part 102 and the treatment tool insertion part 202 into the overtube 300 is not limited to the above-described order, and the endoscope insertion part 102 may be inserted after the treatment tool insertion part 202 is inserted.

Next, a case where the treatment tool insertion part 202 is pushed into the affected part side within the body cavity from the hand side (a case where the treatment tool insertion part moves forward) will be described with reference to FIGS. 26A to 27B.

First, when the treatment tool insertion part 202 has been minutely displaced in the axial direction like a state designated by reference sign 1008 of FIG. 26B from a state designated by reference sign 1006 of FIG. 26A (when a forward and backward movement of a small amplitude has been performed), only the treatment tool insertion part 202 moves forward and backward, and the slider 400 does not move forward and backward. Therefore, since the endoscope insertion part 102 does not move forward and backward, the range of an observation image displayed on the monitor 112 does not change. For this reason, the size of an object to be observed can be prevented from fluctuating according to the minute displacement of the treatment tool insertion part 202, a sense of perspective can be suitably maintained, and a stable observation image can be obtained.

In contrast, when the treatment tool insertion part 202 has been largely displaced in the axial direction like a state designated by reference sign 1010 of FIG. 27B from a state designated by reference sign 1006 of FIG. 27A that is the same state as reference sign 1006 of FIG. 26A (when a forward and backward movement of a large amplitude has been performed), the slider 400 moves forward and backward in an interlocking manner with the forward and backward movement of the treatment tool insertion part 202. In this case, since the endoscope insertion part 102 moves forward and backward, the range of an observation image displayed on the monitor 112 is continuously changed so as to follow the forward and backward movement of the treatment tool insertion part 202. Accordingly, since the size of an object to be observed changes according to the operation of the treatment tool 200, it is possible to simply obtain an image desired by a surgeon.

Additionally, the same applies to a case where the treatment tool insertion part 202 is pulled to the hand side from the affected part side within the body cavity (when the treatment tool insertion part moves backward).

Figure 28A:
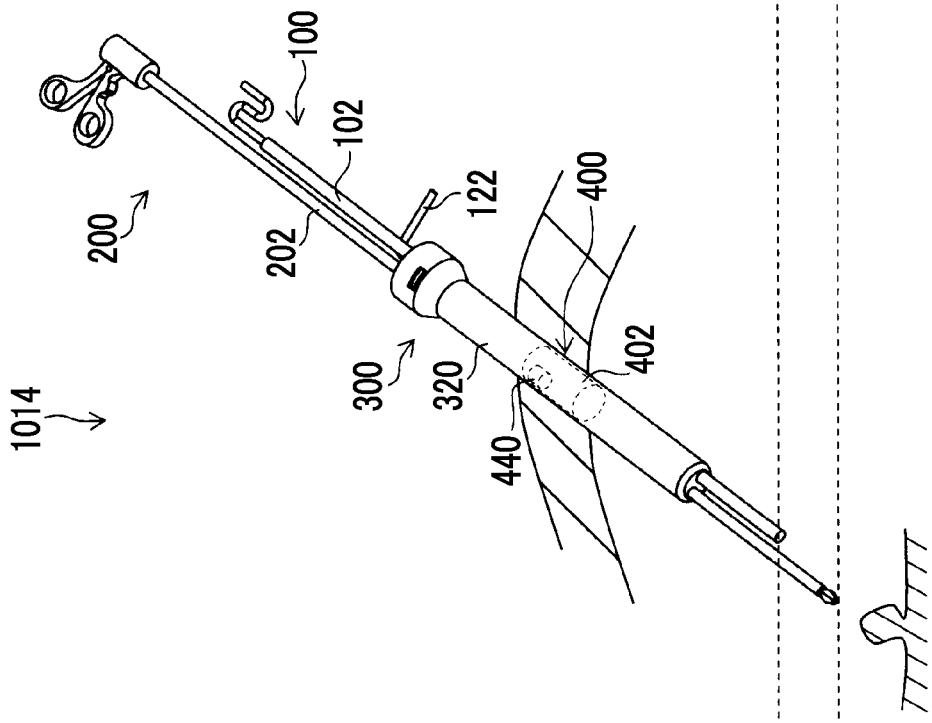
FIGS. 28A and 28B are views illustrating a situation in which the treatment tool insertion part is pulled to the hand side from the affected part side within the body cavity.
Figure 28B:
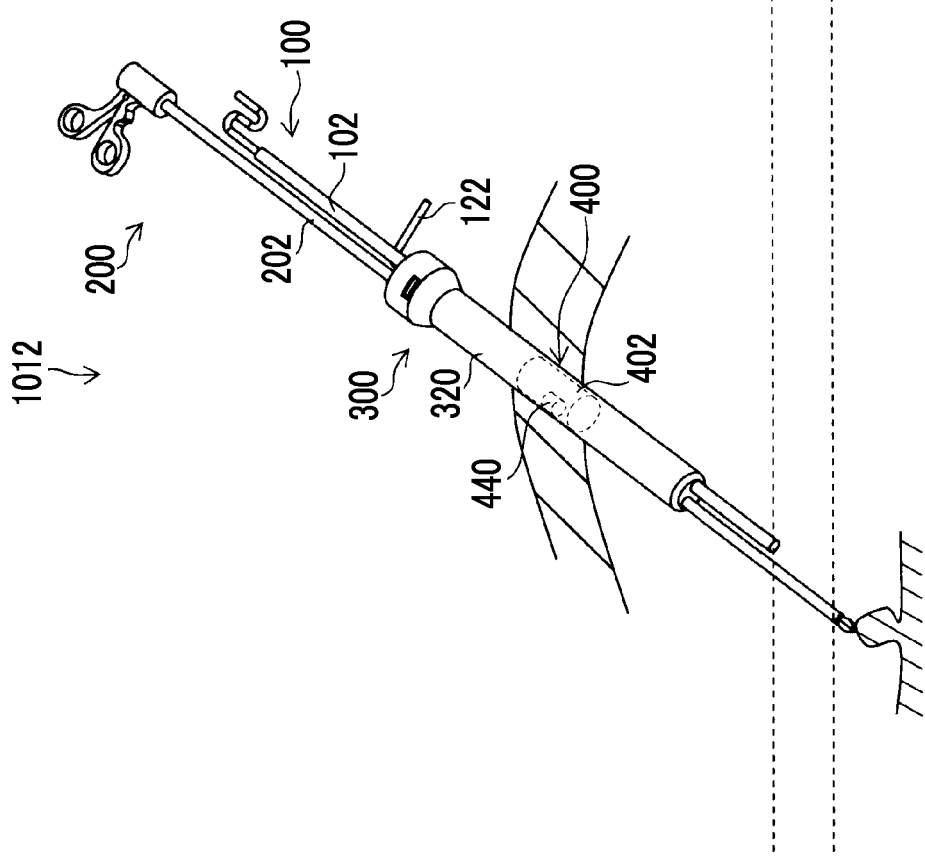

That is, when the treatment tool insertion part 202 has been minutely displaced in the axial direction like a state designated by reference sign 1014 of FIG. 28B from a state designated by reference sign 1012 of FIG. 28A (when a forward and backward movement of a small amplitude has been performed), only the treatment tool insertion part 202 moves forward and backward, and the slider 400 does not move forward and backward. Therefore, since the endoscope insertion part 102 does not move forward and backward, the range of an observation image displayed on the monitor 112 does not change. For this reason, the size of an object to be observed can be prevented from fluctuating according to the minute displacement of the treatment tool insertion part 202, a sense of perspective can be suitably maintained, and a stable observation image can be obtained.

Figure 29A:
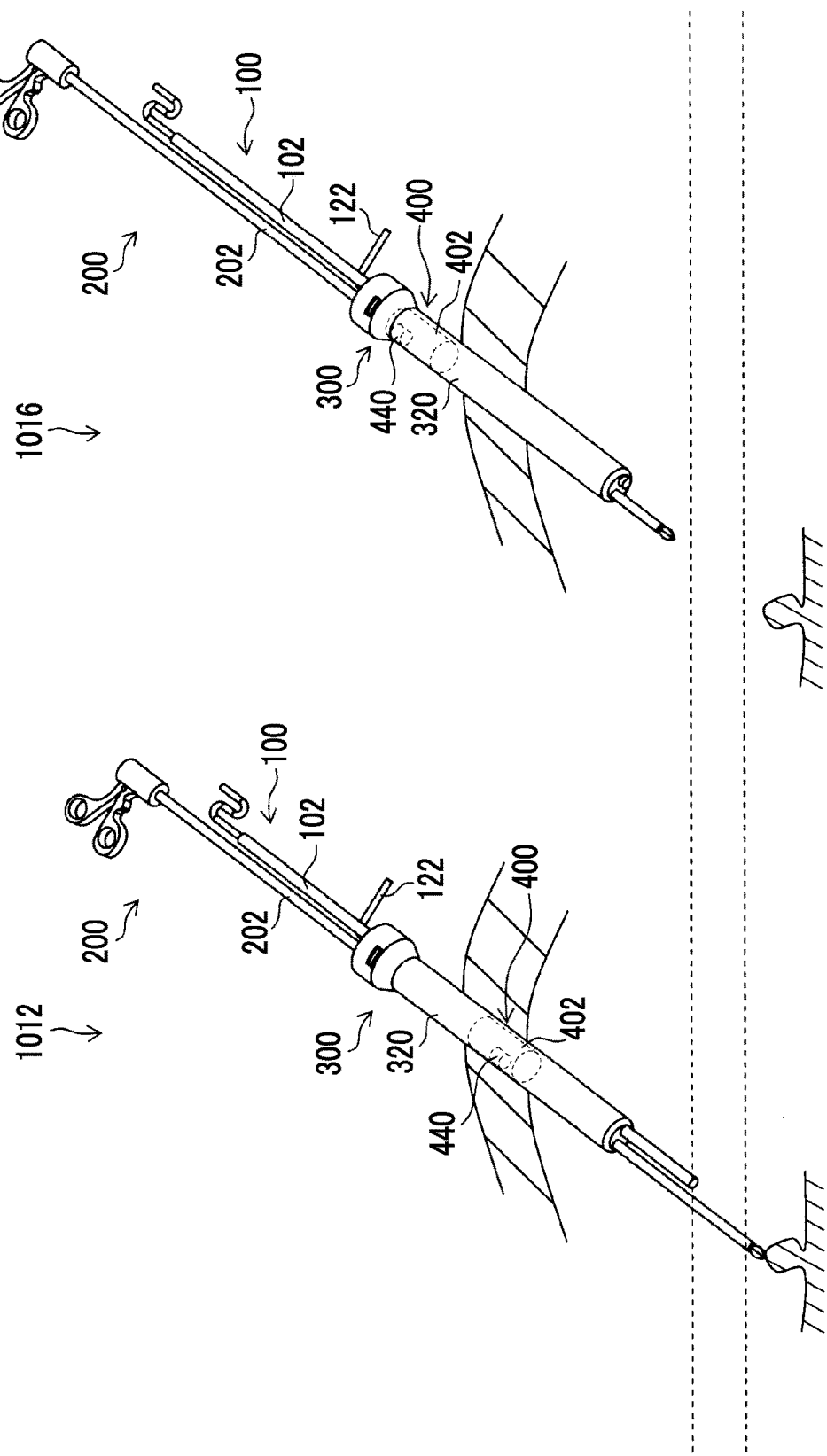
FIGS. 29A and 29B are views illustrating a situation in which the treatment tool insertion part is pulled to the hand side from the affected part side within the body cavity.
Figure 29B:
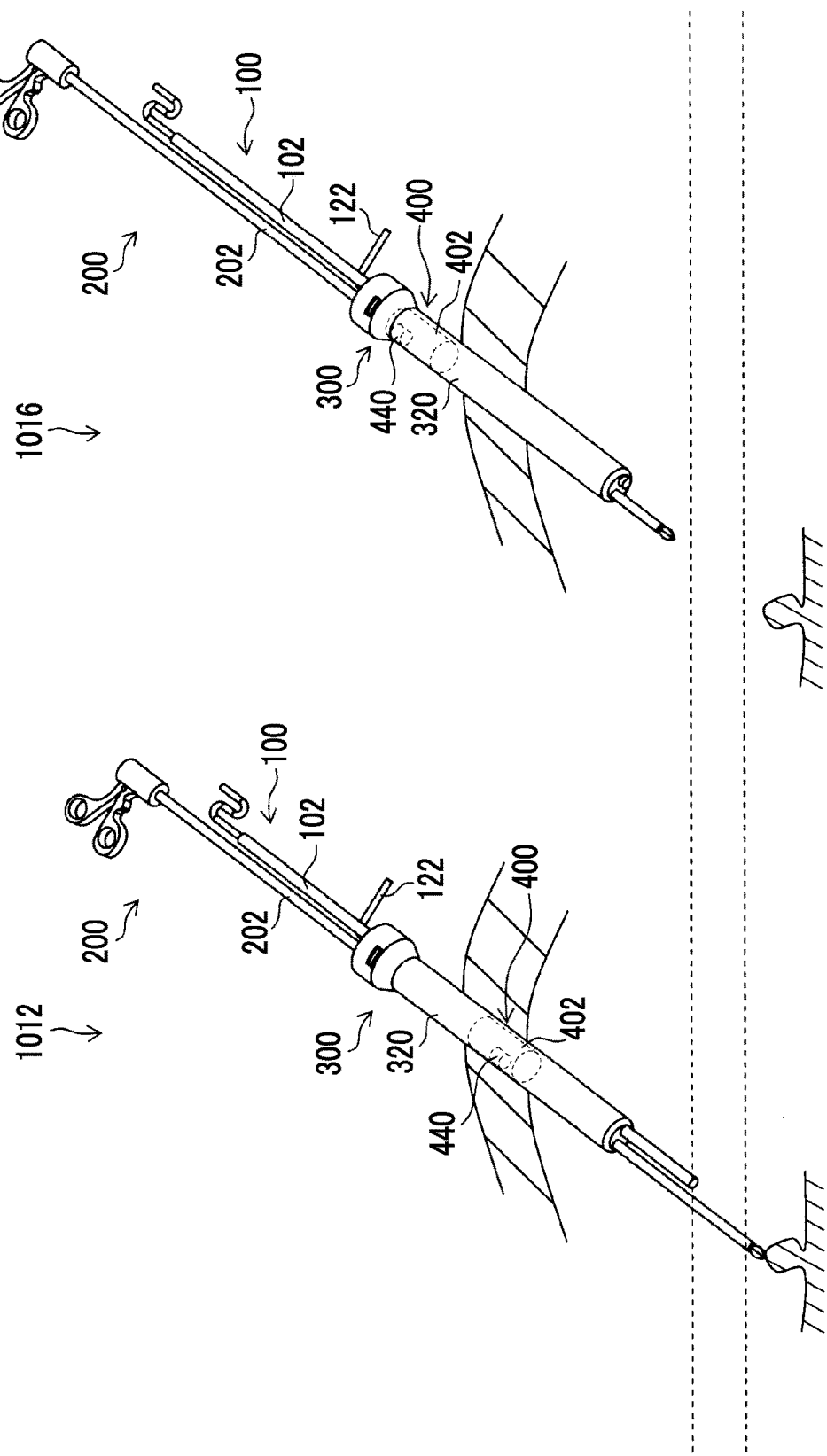

In contrast, when the treatment tool insertion part 202 has been largely displaced in the axial direction like a state designated by reference sign 1016 of FIG. 29B from a state designated by reference sign 1012 of FIG. 29A that is the same state as reference sign 1012 of FIG. 28A (when a forward and backward movement of a large amplitude has been performed), the slider 400 moves forward and backward in an interlocking manner with the forward and backward movement of the treatment tool insertion part 202. In this case, since the endoscope insertion part 102 moves forward and backward, the range of an observation image displayed on the monitor 112 is continuously changed so as to follow the forward and backward movement of the treatment tool insertion part 202. Accordingly, since the size of an object to be observed changes according to the operation of the treatment tool 200, it is possible to simply obtain an image desired by a surgeon.

Next, a case where the endoscope insertion part 102 is extracted from and re-inserted into the overtube 300 for cleaning or the like will be described with reference to FIGS. 30A to 31B.

First, a state designated by reference sign 1018 of FIG. 30A is a state where the endoscope insertion part 102 and the treatment tool insertion part 202 are respectively inserted through the endoscope insertion passage 306 and the treatment tool insertion passage 308 of the overtube 300, and is a state where the endoscope 100 is the endoscope 100 illustrated in FIG. 22 and the slider 400 is coupled in the vicinity of the stepped part 154 of the endoscope insertion part 102.

Figure 31A:
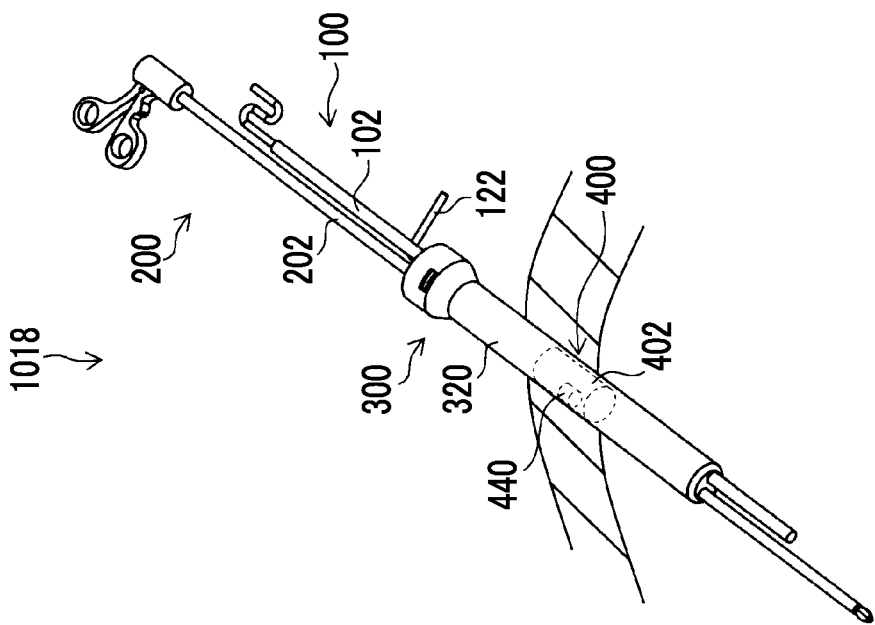
FIGS. 31A and 31B are views illustrating a situation in which the endoscope insertion part is extracted from and re-inserted into the overtube 300.
Figure 31B:
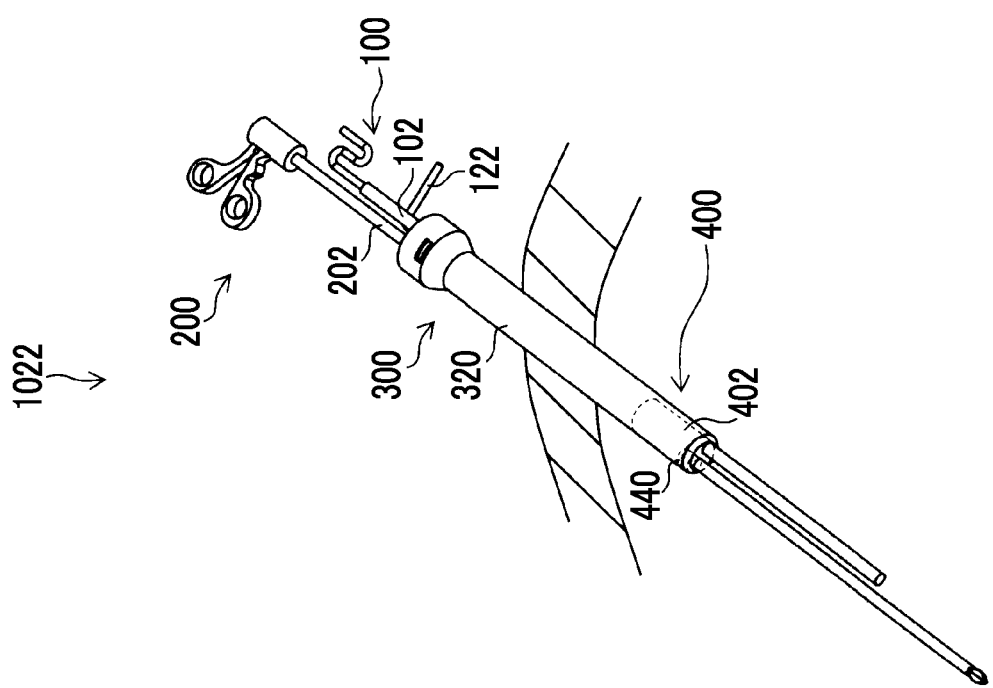

In contrast, when the endoscope insertion part 102 is re-inserted into the endoscope insertion passage 306 of an overtube 300 after the endoscope insertion part 102 has been extracted from the overtube 300 like a state designated by reference sign 1020 of FIG. 30B for cleaning or the like of the endoscope insertion part 102, the slider 400 is pushed by the stepped part 154 and moves to the front end of the movable range thereof, like the state designated by reference sign 1022 of FIG. 31A together with the forward movement of the endoscope insertion part 102. Then, the endoscope insertion part 102 is further moved forward, and the forward movement is stopped when the operating force of the forward movement becomes large. Accordingly, the slider 400 is coupled in the vicinity of the stepped part 154 of the endoscope insertion part 102, and returns to the state designated by reference sign 1018 of part FIG. 31B, that is, the state designated by reference sign 1018 of FIG. 30A.

Although the endoscopic surgical device, the overtube, and the endoscope related to the invention have been described above in detail, the invention is not limited to the above embodiments, and various improvements and modifications may be made without departing from the scope of the invention.

10: endoscopic surgical device
100: endoscope
102: endoscope insertion part
104: operating part
108: processor device
110: light source device
112: monitor
120: pneumoperitoneum device
122: air supply tube
150: smaller-diameter part
152: larger-diameter part
154: stepped part
170: high-friction part
200: treatment tool
202: treatment tool insertion part
204: operating part
206: treatment part
300: overtube
302: base end surface
304: distal end surface
306: endoscope insertion passage
306a: endoscope insertion axis
308: treatment tool insertion passage
308a: treatment tool insertion axis
310: endoscope insertion opening
312: endoscope delivery opening
314: treatment tool insertion opening
316: treatment tool delivery opening
318: air supply connector
320: overtube body
322: outer wall
324: lumen
340: base end cap
342, 344, 350: through-hole
346, 348: valve member
360: distal end cap
362, 364: through-hole
370, 372: guide groove
374, 376: guide plate
400: slider
402: slider body
408, 410: protruding strip
420: endoscope-coupled part
422: treatment tool-coupled part,
424: through-hole
426: pressure-contact member
428: pressure-contact member attachment part
431: left side surface
440: sleeve
444: sleeve body
446: pressure-contact member
448, 450: through-hole
460: guide part
500: inner needle
502, 504: shaft part
506, 508: distal end part
510: head part
512: head part body
514: locking lever
520: axis
532: locking claw
534: locking hole

What is claimed is:

1. An endoscopic surgical device comprising:
an endoscope;
a treatment tool;
an overtube;
a slider provided inside the overtube; and
a sleeve provided inside the overtube,
wherein the slider has a first stopper and a second stopper which are provided separately from each other in a longitudinal direction of the overtube,
wherein the sleeve is slidably located on a first path formed between the first stopper and the second stopper,
wherein the slider has a first holding part configured to hold the endoscope and a second path through which the endoscope is inserted,
wherein the sleeve has a third path through which the treatment tool is inserted and the sleeve comprises a second holding part configured to hold the treatment tool inserted through the third path,
wherein the overtube has a distal end cap that restricts forward and backward movements of the slider with respect to a distal end side of the overtube and a base end cap that restricts forward and backward movements of the slider with respect to a base end side of the overtube,
wherein, in a state where the slider has abutted against the base end cap and the forward and backward movements of the slider with respect to the base end side has been restricted, when a length from a coupling position of the endoscope, to which the first holding part is coupled, to a distal end position of the overtube in an axial direction of the overtube is defined as L and a length from the coupling position to a distal end position of the endoscope is defined as Ls, the coupling position is set so as to satisfy a following formula $$Ls \leq L.$$

2. The endoscopic surgical device according to claim 1, wherein the endoscope includes a smaller-diameter part that is arranged on the distal end side, and a larger-diameter part that is connected to a base end side of the smaller-diameter part, the smaller-diameter part is not coupled to the first holding part, and the larger-diameter part is configured to be engageable with the first holding part.

3. The endoscopic surgical device according to claim 2, wherein the first holding part is provided with a frictional engagement part that frictionally engages with the larger-diameter part.

4. The endoscopic surgical device according to claim 1, wherein the endoscope is made of a high-friction member having a higher frictional coefficient at the coupling position than at other positions where the first holding part is not coupled, and
wherein the first holding part is provided with a frictional engagement part that frictionally engages with the high-friction member.

5. The endoscopic surgical device according to claim 1, wherein the sleeve is configured so as to be rotatable around an axis of the treatment tool with respect to the slider.

6. The endoscopic surgical device according to claim 1, wherein the slider is configured so as to be non-rotatable around an axis of the treatment tool with respect to the overtube.

7. The endoscopic surgical device according to claim 1, wherein a following formula is satisfied when a fixing force for fixing the first holding part to the endoscope is defined as F1 and a fixing force for fixing the second holding part to the treatment tool is defined as F2

$$F1 > F2.$$

8. The endoscopic surgical device according to claim 1, further comprising:
- a first valve member that contacts the endoscope when the endoscope is inserted through the second path and that secures airtightness within a body cavity; and
- a second valve member that contacts the treatment tool when the treatment tool is inserted through the third path and that secures airtightness within the body cavity,
- wherein following formulas are satisfied when a fixing force for fixing the first holding part to the endoscope is defined as F1, a fixing force for fixing the second holding part to the treatment tool is defined as F2, and a frictional force that the endoscope receives from the first valve member when the endoscope moves forward and backward is defined as F3

$$F1 > F3$$

$$F2 > F3.$$

9. The endoscopic surgical device according to claim 1, wherein the sleeve is located inside of the slider.

10. An overtube guiding an endoscope and a treatment tool into a body cavity, the overtube comprising:
- a slider provided inside the overtube; and
- a sleeve provided inside the overtube,
- wherein the slider has a first stopper and a second stopper which are provided separately from each other in a longitudinal direction of the overtube,
- wherein the sleeve is slidably located on a first path formed between the first stopper and the second stopper,
- wherein the slider has a first holding part configured to hold the endoscope and a second path through which the endoscope is inserted,
- wherein the sleeve has a third path through which the treatment tool is inserted and the sleeve comprises a second holding part configured to hold the treatment tool inserted through the third path,
- wherein the overtube has a distal end cap that restricts forward and backward movements of the slider with respect to a distal end side of the overtube and a base end cap that restricts forward and backward movements of the slider with respect to a base end side of the overtube,
- wherein, in a state where the slider has abutted against the base end cap and the forward and backward movements of the slider with respect to the base end side has been restricted, when a length from a coupling position of the endoscope, to which the first holding part is coupled, to a distal end position of the overtube in an axial direction of the overtube is defined as L and a length from the coupling position to a distal end position of the endoscope is defined as Ls, the coupling position is set so as to satisfy a following formula $$Ls \geq L.$$

11. The overtube according to claim 10,
wherein the endoscope includes a smaller-diameter part that is arranged on the distal end side, and a larger-diameter part that is connected to a base end side of the smaller-diameter part, the first holding part is not coupled to the smaller-diameter part, and the first holding part is configured to be engageable with the larger-diameter part.

12. The overtube according to claim 11,
wherein the first holding part is provided with a frictional engagement part that frictionally engages with the larger-diameter part.

13. The overtube according to claim 10,
wherein the endoscope is made of a high-friction member having a higher frictional coefficient at the coupling position than at other positions where the first holding part is not coupled, and
wherein the first holding part is provided with a frictional engagement part that frictionally engages with the high-friction member.

14. The overtube according to claim 10, wherein the sleeve is located inside of the slider.

* * * * *